United States Patent
Liu

(10) Patent No.: US 11,963,726 B2
(45) Date of Patent: Apr. 23, 2024

(54) SURGICAL OPERATION MONITORING METHOD AND DEVICE

(71) Applicant: BOE Technology Group Co., Ltd., Beijing (CN)

(72) Inventor: Huichao Liu, Beijing (CN)

(73) Assignee: BOE Technology Group Co., Ltd., Beijing (CN)

(*) Notice: Subject to any disclaimer, the term of this patent is extended or adjusted under 35 U.S.C. 154(b) by 440 days.

(21) Appl. No.: 17/412,131

(22) Filed: Aug. 25, 2021

(65) Prior Publication Data

US 2022/0117667 A1 Apr. 21, 2022

(30) Foreign Application Priority Data

Oct. 15, 2020 (CN) .......................... 202011101760.3

(51) Int. Cl.
*A61B 34/20* (2016.01)
*A61B 34/30* (2016.01)
*A61G 13/02* (2006.01)

(52) U.S. Cl.
CPC .............. *A61B 34/20* (2016.02); *A61B 34/30* (2016.02); *A61G 13/02* (2013.01); *A61B 2034/2046* (2016.02)

(58) Field of Classification Search
CPC . A61B 34/20; A61B 34/30; A61B 2034/2046; A61B 2034/2055; A61B 90/37; A61B 2034/2057; A61B 2034/2068; A61B 2034/305; A61B 2090/373; A61G 13/02
See application file for complete search history.

(56) References Cited

U.S. PATENT DOCUMENTS

| 2018/0353253 A1* | 12/2018 | Bowling | ................ B25J 9/1633 |
| 2019/0142533 A1* | 5/2019 | Itkowitz | ................ A61B 34/25 |
| | | | 700/254 |
| 2020/0008884 A1* | 1/2020 | Lavallee | ................ A61B 34/30 |

FOREIGN PATENT DOCUMENTS

| CN | 104363850 B | * | 8/2017 | ............. A61B 34/30 |
| CN | 107072725 A | | 8/2017 | |
| CN | 108186120 A | | 6/2018 | |
| CN | 110430836 A | | 11/2019 | |
| CN | 110997247 A | | 4/2020 | |
| CN | 111374777 A | | 7/2020 | |
| CN | 111714210 A | | 9/2020 | |
| EP | 3733110 A1 | | 11/2020 | |

(Continued)

OTHER PUBLICATIONS

CN202011101760.3 first office action and search report.

*Primary Examiner* — Ziaul Karim
(74) *Attorney, Agent, or Firm* — IPro, PLLC

(57) ABSTRACT

A surgical operation monitoring method applied to a surgical operation monitoring system comprises: acquiring a position of a surgical site of a surgical object at a first moment; under the condition that the position of the surgical site at the first moment exceeds a moving range of an actuating end of a mechanical arm, determining an allowable moving range of the surgical site at the first moment; and under the condition that the allowable moving range of the surgical site at the first moment and a moving range of the actuating end of the mechanical arm have an overlapping range, controlling a driver to drive a support body to move so that the support body drives the surgical site to move into the overlapping range.

17 Claims, 11 Drawing Sheets

(56) References Cited

FOREIGN PATENT DOCUMENTS

| | | | |
|---|---|---|---|
| JP | 2012005557 | A | 1/2012 |
| WO | 2010068005 | A2 | 6/2010 |

\* cited by examiner

SURGICAL OPERATION MONITORING METHOD AND DEVICE

The disclosure claims the priority of a Chinese patent application filed in the China National Intellectual Property Administration on Oct. 15, 2020 with an application number of 202011101760.3 and a title of "Surgical Operation Monitoring Method and Device", the entire contents of which are hereby incorporated by reference.

TECHNICAL FIELD

The disclosure relates to the technical field of surgical robots, in particular to a surgical operation monitoring method and device.

BACKGROUND

With the development of science and technology, robots are increasingly used to complete difficult and dangerous tasks for people. Surgical robots can not only help doctors accurately locate a surgical site, but also minimize surgical injuries, improve the accuracy and quality of disease diagnosis and surgical treatment, improve surgical safety, and shorten surgical time. In recent years, master-slave telecontrol has been used in various surgical operations.

SUMMARY

The disclosure provides a surgical operation monitoring method and device.

The disclosure adopts the following technical solution:
an embodiment of the disclosure provides a surgical operation monitoring method, which is applied to a surgical operation monitoring system. The surgical operation monitoring system comprises a surgical support device and a surgical robot. The surgical support device comprises a stand, a support body mounted on the stand and a driver configured to drive the support body to move relative to the stand. The support body is configured to support a surgical object, and the surgical robot comprises mechanical arms with actuating ends. The surgical operation monitoring method comprises the following steps:

acquiring a position of a surgical site of the surgical object at a first moment;

under the condition that the position of the surgical site at the first moment exceeds a moving range of the actuating end of the mechanical arm, determining an allowable moving range of the surgical site at the first moment, which is a range within which the driver can drive the support body to move so that the support body drives the surgical site to move at the first moment; and under the condition that the allowable moving range of the surgical site at the first moment and the moving range of the actuating end of the mechanical arm have an overlapping range, controlling the driver to drive the support body to move so that the support body drives the surgical site to move into the overlapping range.

Optionally, the method further comprises:
controlling the actuating end of the mechanical arm to move to a position corresponding to the position of the surgical site at the first moment, under the condition that the position of the surgical site at the first moment does not exceed the moving range of the actuating end of the mechanical arm and the surgical site deviates from the actuating end of the mechanical arm at the first moment.

Optionally, the method further comprises:
controlling the actuating end of the mechanical arm to perform operation according to a first surgical path, under the condition that the position of the surgical site at the first moment does not exceed the moving range of the actuating end of the mechanical arm and the surgical site does not deviate from the actuating end of the mechanical arm at the first moment; and correcting the first surgical path according to a position corresponding to the position of the surgical site at the first moment to obtain a second surgical path, under the condition that the position of the surgical site at the first moment does not exceed the moving range of the actuating end of the mechanical arm and the surgical site deviates from the actuating end of the mechanical arm at the first moment, and controlling the actuating end of the mechanical arm to perform operation according to the second surgical path after the actuating end of the mechanical arm moves to the position corresponding to the position of the surgical site at the first moment.

Optionally, the method further comprises:
acquiring a first deviation of the surgical site from the actuating end of the mechanical arm at the first moment;

wherein, if the first deviation is within an operable range, the surgical site does not deviate from the actuating end of the mechanical arm; and if the first deviation is beyond the operable range, the surgical site deviates from the actuating end of the mechanical arm.

Optionally, the method further comprises:
acquiring a position of the actuating end of the mechanical arm at the first moment; and controlling the driver to drive the support body to move to make the support body drive the surgical site to move into the overlapping range, under the condition that the position of the surgical site at the first moment exceeds the moving range of the actuating end of the mechanical arm and the position of the actuating end of the mechanical arm at the first moment is within the overlapping range, comprising: controlling the driver to drive the support body to move, so that the support body drives the surgical site to move to a position corresponding to the position of the actuating end of the mechanical arm at the first moment.

Optionally, the method further comprises:
controlling the actuating end of the mechanical arm to move to a first position within the overlapping range, under the condition that the position of the actuating end of the mechanical arm at the first moment is beyond the overlapping range; and controlling the driver to drive the support body to move so that the support body drives the surgical site to move into the overlapping range comprises:

controlling the driver to drive the support body to move, so that the support body drives the surgical site to move to a second position within the overlapping range, the second position being a position corresponding to the first position.

Optionally, the method further comprises:
controlling the actuating end of the mechanical arm to perform operation according to a first surgical path after the support body drives the surgical site to move to the position corresponding to the position of the actuating end of the mechanical arm at the first moment under the condition that the position of the actuating end of the mechanical arm is located within the overlapping range; and correcting the first surgical path according to the first position to obtain a third surgical path and controlling the actuating end of the mechanical arm to perform operation according to the third surgical path, under the condition that the position of the actuating end of the mechanical arm at the first moment is beyond the overlapping range.

Optionally, the surgical operation monitoring system further comprises an alarm, and the surgical operation monitoring method further comprises:

controlling the mechanical arm to stop moving and controlling the alarm to give an alarm, under the condition that the position of the surgical site exceeds the moving range of the actuating end of the mechanical arm and the allowable moving range of the surgical site at the first moment and the moving range of the actuating end of the mechanical arm do not have an overlapping range.

Optionally, the number of the drivers is at least three, and the at least three drivers comprise a first driver, a second driver and a third driver; the first driver is configured to drive the support body to move in a first direction, the second driver is configured to drive the support body to move in a second direction, the third driver is configured to drive the support body to move in a third direction, and the first direction, the second direction and the third direction are perpendicular to each other;

acquiring the position of the surgical site at the first moment comprises:

acquiring the coordinates of the surgical site at the first moment; and determining the allowable moving range of the surgical site at the first moment comprises:

acquiring a first allowable deviation distance in the first direction, a second allowable deviation distance in the second direction and a third allowable deviation distance in the third direction of the support body at the first moment; and calculating the coordinates of the surgical site after the surgical site deviates by the first allowable deviation distance in the first direction, the second allowable deviation distance in the second direction and the third allowable deviation distance in the third direction, according to the first allowable deviation distance, the second allowable deviation distance and the third allowable deviation distance, and the coordinates of the surgical site at the first moment, to determine that a range defined by the coordinates of the surgical site after the surgical site deviates by the first allowable deviation distance in the first direction, the second allowable deviation distance in the second direction and the third allowable deviation distance in the third direction is the allowable movement range.

Optionally, the surgical operation monitoring system further comprises at least three position sensors, and the at least three position sensors comprise a first position sensor, a second position sensor and a third position sensor which are electrically connected with the processor; the first position sensor is configured to detect a first deviation distance of the support body relative to a reference position in the first direction, the second position sensor is configured to detect a second deviation distance of the support body relative to the reference position in the second direction, and the third position sensor is configured to detect a third deviation distance of the support body relative to the reference position in the third direction; and acquiring the first allowable deviation distance in the first direction, the second allowable deviation distance in the second direction and the third allowable deviation distance in the third direction of the support body at the first moment comprises:

receiving the first deviation distance, the second deviation distance and the third deviation distance detected by the first position sensor, the second position sensor and the third position sensor; and according to the received first deviation distance, second deviation distance and third deviation distance, and a first deviatable distance in the first direction, a second deviatable distance in the second direction and a third deviatable distance in the third direction of the support body when the support body is located at the reference position, calculating the first allowable deviation distance in the first direction, the second allowable deviation distance in the second direction and the third allowable deviation distance in the third direction of the support body at the first moment.

Another embodiment of the disclosure provides a surgical operation monitoring device, comprising: a processor and a memory, wherein the memory is configured to store computer program instructions; and when the computer program instructions are executed by the processor, the surgical operation monitoring device is caused to implement the surgical operation as described above.

Another embodiment of the disclosure provides a computer readable storage medium, which stores computer program instructions, wherein when the computer program instructions are run on a surgical operation monitoring device, the surgical operation monitoring device is enabled to execute the surgical operation as described above.

The above description is only an overview of the technical solution of this disclosure, which can be implemented according to the contents of the specification in order to understand the technical means of this disclosure more clearly, and in order to make the above and other objects, features and advantages of this disclosure more obvious and understandable, the detailed description of this disclosure will be given below.

BRIEF DESCRIPTION OF THE DRAWINGS

In order to explain the technical solution in the embodiments of the disclosure more clearly, the drawings used in the description of the embodiments will be briefly introduced below.

Obviously, the drawings in the following description are only some embodiments of the disclosure, and for those of ordinary skill in the art, other drawings can be obtained according to these drawings without paying creative labor.

DETAILED DESCRIPTION

Figure 1:
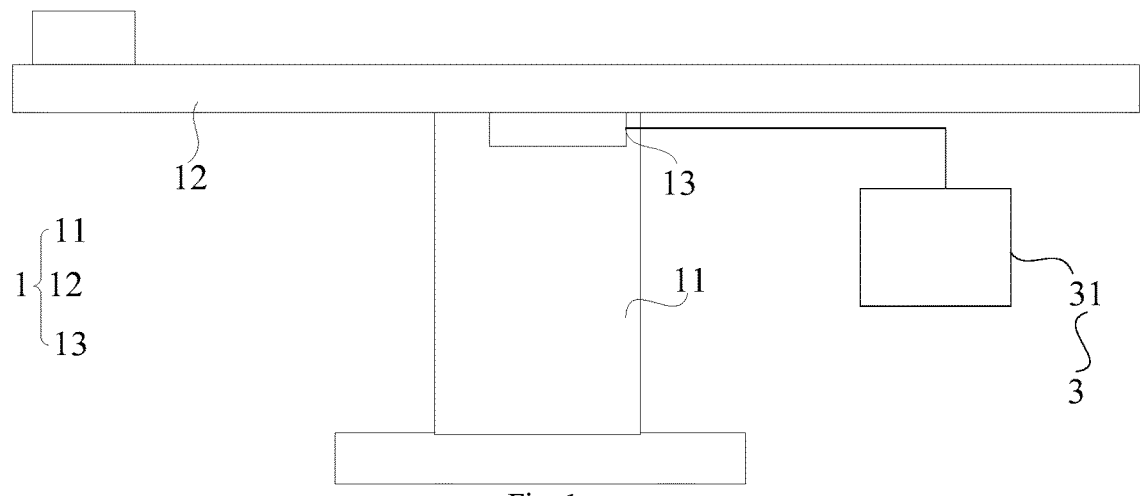
FIG. 1 is a structural diagram of a surgical support device provided by an embodiment of the disclosure.

The technical solution in the embodiments of the disclosure will be clearly and completely described below with reference to the drawings in the embodiments of the disclosure. Obviously, the described embodiments are only part of the embodiments of the disclosure, not all of the embodiments. Based on the embodiments in the disclosure, all other embodiments obtained by those of ordinary skill in the art without creative labor are within the scope of protection of the disclosure.

In the description of the disclosure, it should be noted that the orientation or position relationship indicated by the terms "centric", "upper", "lower", "front", "rear", "left", "right", "vertical", "horizontal", "top", "bottom", "inner" and "outer" are based on the orientation or position relationship shown in the drawings, only for convenience of describing the disclosure and simplifying the description, and do not indicate or imply that the indicated device or element must have a specific orientation, or be constructed and operate in a specific orientation, and therefore cannot be understood as a limitation of the disclosure. In the description of the disclosure, unless otherwise specified, "a plurality of" refers to two or more.

Unless otherwise specified in the context, throughout the specification and claims, the term "comprise" and other forms thereof such as the third person singular form "comprises" and the present participle form "comprising" are interpreted as open and inclusive, that is, "including, but not limited to". In the description of the specification, the terms "one embodiment", "some embodiments", "exemplary embodiments", "example", "specific example" or "some examples", etc., are intended to indicate that specific features, structures, materials or characteristics related to this embodiment or example are included in at least one embodiment or example of the disclosure. Schematic representations of the above terms do not necessarily refer to the same embodiment or example. In addition, the specific features, structures, materials or characteristics described may be included in any one or more embodiments or examples in any suitable manner.

Hereinafter, the terms "first" and "second" are only used for descriptive purposes, and cannot be understood as indicating or implying relative importance or implicitly indicating the number of indicated technical features. Therefore, the features defined with "first" and "second" may include one or more of the features explicitly or implicitly.

In describing some embodiments, expressions like "coupled" and "connected" and their derivatives may be used. For example, the term "connected" may be used when describing some embodiments to indicate that two or more components have direct physical or electrical contact. For another example, the term "coupled" may be used when describing some embodiments to indicate that two or more components have direct physical or electrical contact. However, the term "coupled" or "communicatively coupled" may also mean that two or more components are not in direct contact with each other, but still cooperate or interact with each other. The embodiments disclosed herein are not necessarily limited to the contents herein.

The expression "at least one of A, B and C" has the same meaning as the expression "at least one of A, B or C" and includes the following combinations of A, B and C: only A, only B, only C, the combination of A and B, the combination of A and C, the combination of B and C, and the combination of A, B and C.

The expression "A and/or B" includes the following three combinations: only A, only B, and the combination of A and B.

As used herein, the term "if" is optionally interpreted as "when" or "in response to the determination of" or "in response to the detection of", depending on the context. Similarly, depending on the context, the phrases "if it is determined that . . . " or "if it is detected that [stated condition or event]" are optionally interpreted as "when it is determined that" or "in response to the determination of" or "when it is detected that [stated condition or event]" or "in response to the detection of [stated condition or event]".

The phrase "used to" or "configured to" used herein has an open and inclusive meaning, which does not exclude devices used to or configured to perform additional tasks or steps.

In addition, the meaning of "based on" is open and inclusive because a process, step, calculation or other action "based on" one or more of the stated conditions or values may be based on additional conditions or values beyond the stated values in practice.

Figure 2:
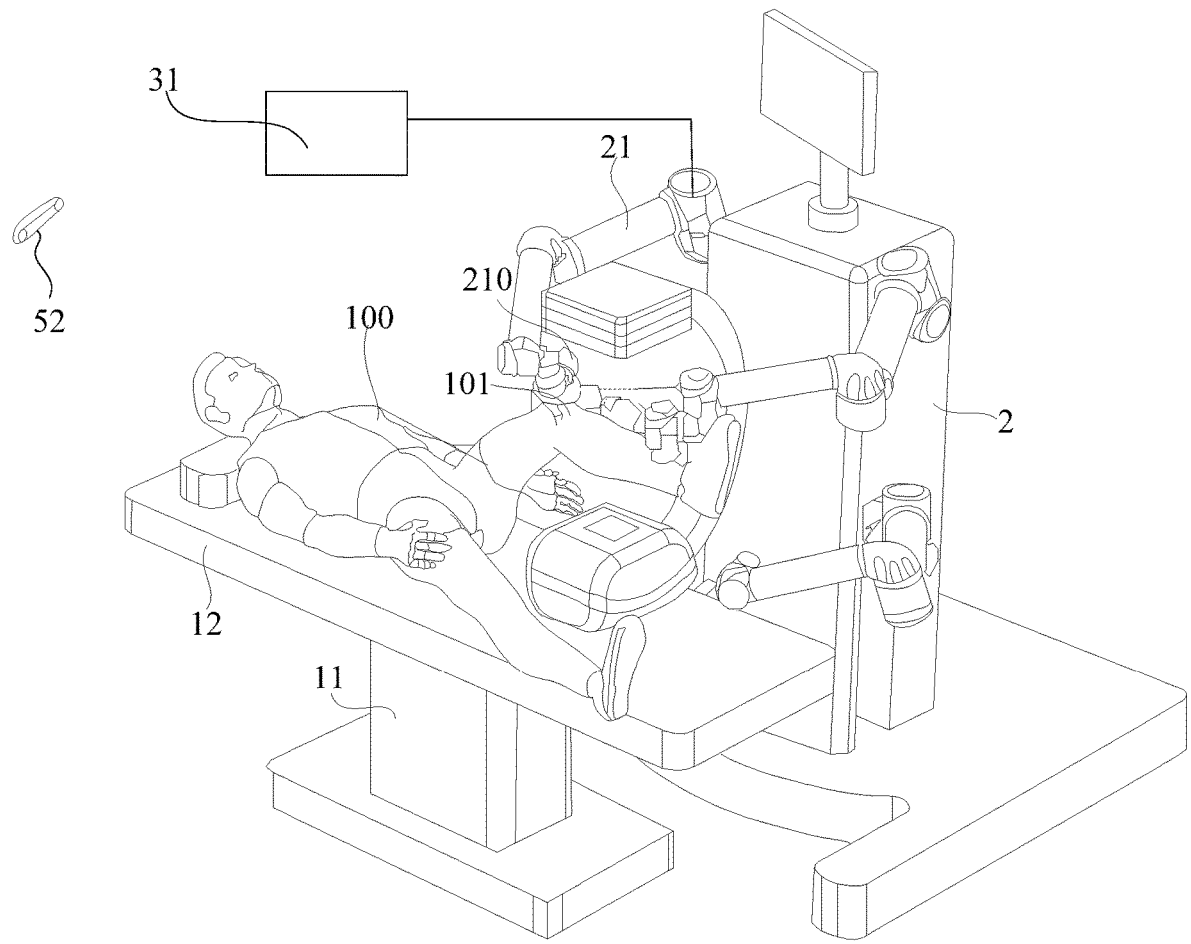
FIG. 2 is a structural diagram of a surgical operation monitoring system provided by an embodiment of the disclosure.

An embodiment of the disclosure provides a surgical operation monitoring system. Referring to FIGS. 1 and 2, the surgical operation monitoring system comprises a surgical support device 1, a surgical robot 2 and a surgical operation monitoring device 3. The surgical support device 1 comprises a stand 11, a support body 12 mounted on the stand 11 and a driver 13 configured to drive the support body 12 to move relative to the stand 11, and the support body 12 is configured to support a surgical object 100. The surgical robot 2 comprises mechanical arms 21 with actuating ends 210.

Figure 3:
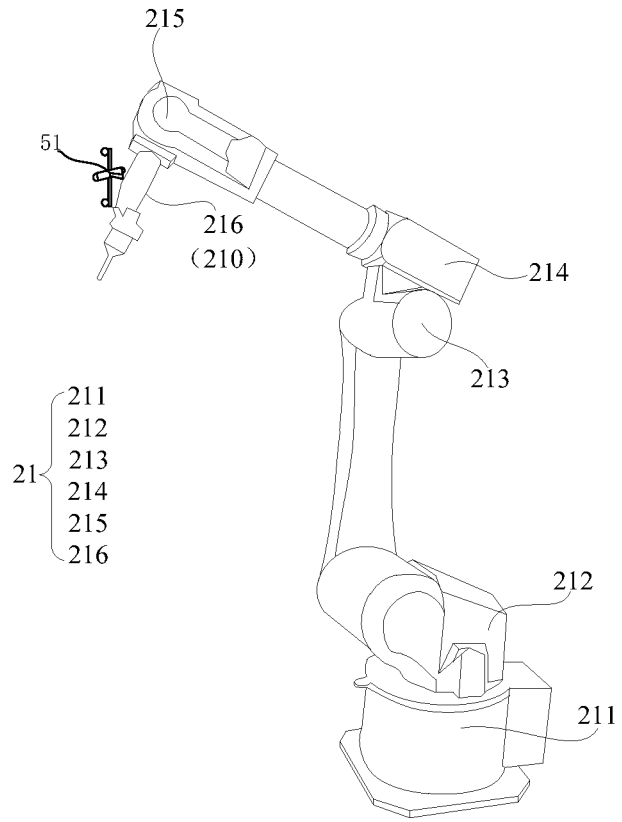
FIG. 3 is a structural diagram of a mechanical arm provided by an embodiment of the disclosure.

The surgical support device 1 may be an operating bed or an operating seat by way of example. The surgical robot 2 may be a mechanical device capable of performing surgical operations by imitating human actions under control. Assuming that the surgical robot 2 is a six-axis robot, as shown in FIG. 3, the mechanical arm 21 may comprise a first axis 211, a second axis 212, a third axis 213, a fourth axis 214, a fifth axis 215 and a sixth axis 216. The first axis 211 is connected to a base, mainly bears the weight of the axis above, and rotates axially relative to the base. The second axis 212 controls the front-and-back swing of the mechanical arm and realizes the up-and-down movement of the whole main arm. The third axis 213 also controls the front-and-back swing of the mechanical arm, but a swing range of the third axis is smaller than that of the second axis 212. The fourth axis 214 controls a circular tube on the mechanical arm 21 to rotate freely, and its moving range is equivalent to that of a human forearm. The fifth axis 215 controls the up-and-down turning action for fine adjustment, which is usually an action that turns a product over after the product is grabbed. The sixth axis 216 is an end part, that is, the actuating end 210 in this embodiment, which is used to connect the tools used in surgery (such as scalpel, cutter and drill) and can rotate by 360°.

Figure 4:
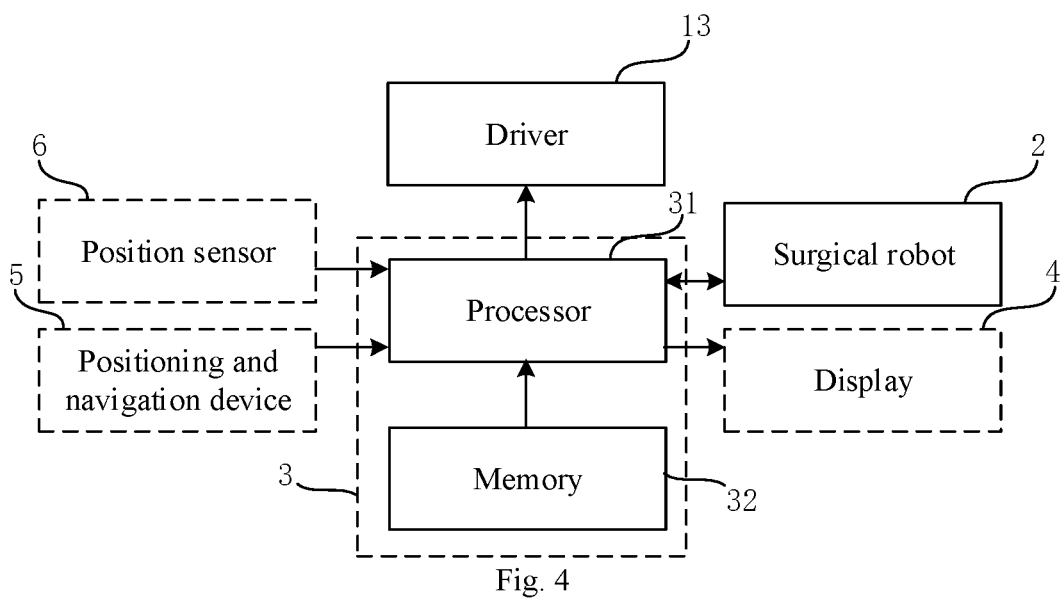
FIG. 4 is a structural block diagram of a surgical operation monitoring system provided by an embodiment of the disclosure.

The surgical operation monitoring device 3 may be an electronic device such as a computer. As shown in FIG. 4, the surgical operation monitoring device may comprise a processor 31 and a memory 32, and the memory 32 is configured to store computer program instructions. When the computer program instructions are executed by the processor 31, the surgical operation monitoring device 3 is caused to implement the surgical operation monitoring method.

For example, as shown in FIG. 4, in addition to the surgical operation monitoring device 3, the surgical robot 2 and the surgical support device 1, the surgical operation monitoring system may comprise a display 4, a positioning and navigation device 5 mentioned later, a position sensor 6, an alarm, etc.

As shown in FIGS. 1, 2 and 4, the surgical operation monitoring device 3 may comprise a processor 31, a memory 32, a communication interface and the like connected by a bus.

The memory 32 can store computer programs and data, and can be a high-speed random access memory or a non-volatile memory, such as a magnetic disk memory device, a flash memory device or other volatile solid-state memory devices.

The processor 31 can be connected to the memory 32, and can run or execute the computer programs stored in the memory 32 to make the surgical operation monitoring device 3 realize various functions. The processor 31 may be one or more central processing units (CPU), microprocessors, application-specific integrated circuits (ASIC) or integrated circuits for controlling the execution of programs in some embodiments of the disclosure. The CPU can be either a single-CPU or a multi-CPU. Here, a processor 31 may refer to one or more devices, circuits or processing cores for processing data (e.g., computer program instructions).

The communication interface is configured to communicate with various external devices by various communication methods, and is connected with the processor 31 to send data or commands to the external devices or receive data or commands sent by the external devices under the control of the processor 31. The communication interface can be a transceiver, a transceiver circuit, a transmitter, a receiver, etc. For example, the communication interface can be a wireless communication device such as a Wireless-Fidelity (Wi-Fi) chip and a Bluetooth chip, or a wired communication device such as a universal serial bus (USB) interface.

For example, the processor 31 can be communicatively connected with the surgical support device 1 through the communication interface, and send a control instruction to the surgical support device 1 to control the driver 13 in the surgical support device 1 to work, so that the driver 13 drives the support body 12 to move. The processor 31 can also be communicatively connected with the surgical robot 2 through the communication interface, and send a control instruction to the surgical robot 2 to control the mechanical arm 21 of the surgical robot 2 to move, so as to control a position of the actuating end 210 of the mechanical arm 21. The processor 31 can also acquire the position of the surgical support device 1 detected by the position sensor 6 on the surgical support device 1, so as to send a control instruction to the driver 13 of the surgical support device according to the position of the surgical support device 1. The processor 31 can also be communicatively connected with the positioning and navigation device 5 through the communication interface, and is used for acquiring the positions of a surgical site 101 and the actuating end 210 of the mechanical arm 21 detected by the positioning and navigation device 5, so as to control the positions of the actuating end 210 of the mechanical arm 21 and the surgical site 101. The processor 31 can also be connected with the display 4 to control the display 4 to display images.

The communication interface may only be a transmitting interface or a receiving interface, or may be a bidirectional communication interface. When the communication interface is a bidirectional communication interface, the communication interface can be used as both a transmitting interface and a receiving interface, and has dual functions of sending and receiving signals.

Figure 5:
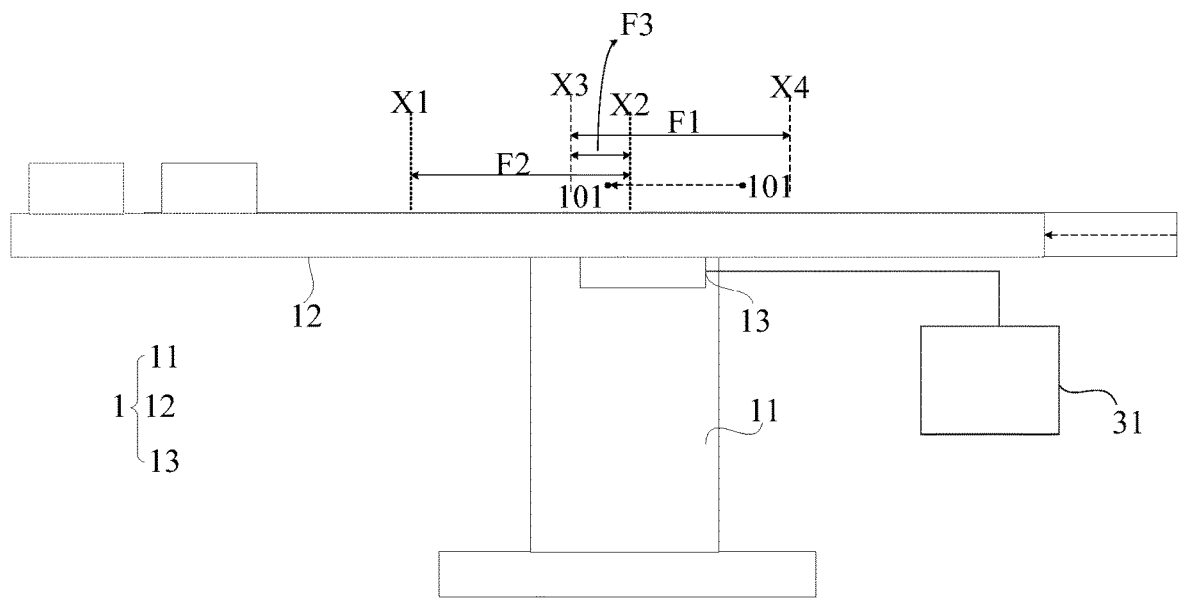
FIG. 5 is a structural diagram of a surgical support device moving in a first direction provided by an embodiment of the disclosure.

Based on the above examples, in some embodiments, as shown in FIG. 5, the processor 31 is configured to acquire a position of the surgical site 101 (as shown by the small black dot in FIG. 5) of the surgical object 100 at a first moment. When the surgical object 100 moves in surgery, and the position of the surgical site 101 exceeds a moving range F1 of the actuating end 210 of the mechanical arm 21, an allowable moving range F2 of the surgical site 101 at the first moment is determined; and under the condition that the allowable moving range F2 of the surgical site 101 at the first moment and the moving range F1 of the actuating end 210 of the mechanical arm 21 have an overlapping range F3, the driver 13 is controlled to drive the support body 12 to move so that the support body 12 drives the surgical site 101 to move into the overlapping range F3. The allowable moving range F2 of the surgical site 101 at the first moment is the range within which the driver 13 can drive the support body 12 to move so that the support body 12 drives the surgical site 101 to move at the first moment.

In surgery, the posture of the surgical object 100 may change, thus causing a change in the position of the surgical site 101. In view of this, the first moment can be any moment in surgery.

The moving range F1 of the actuating end 210 of the mechanical arm 21 can be stored in the processor 31 in advance, or can be obtained by detection and calculation.

In some embodiments, as shown in FIGS. 2, 3, 4 and 6, the surgical operation monitoring system further comprises a positioning and navigation device 5 electrically connected with the processor 31, and the positioning and navigation device 5 is configured to acquire the positions of the surgical site 101 and the actuating end 210 of the mechanical arm 21 in real time and send the acquired positions of the surgical site 101 and the actuating end 210 of the mechanical arm 21 to the processor 31.

The position of the actuating end 210 of the mechanical arm 21 can be acquired in real time by the positioning and navigation device 5, and the moving range F1 of the actuating end 210 of the mechanical arm 21 can be obtained by controlling the motion of the mechanical arm 21 by the processor 31 and detecting a position that the actuating end 210 of the mechanical arm 21 can reach when the mechanical arm 21 moves by the positioning and navigation device 5. The position of the surgical site 101 can be acquired in real time by the positioning and navigation device 5, and whether the position of the surgical site 101 exceeds the moving range F1 of the actuating end 210 of the mechanical arm 21 can be determined by comparing the position of the surgical site 101 with the moving range F1 of the actuating end 210 of the mechanical arm 21.

Figure 6:
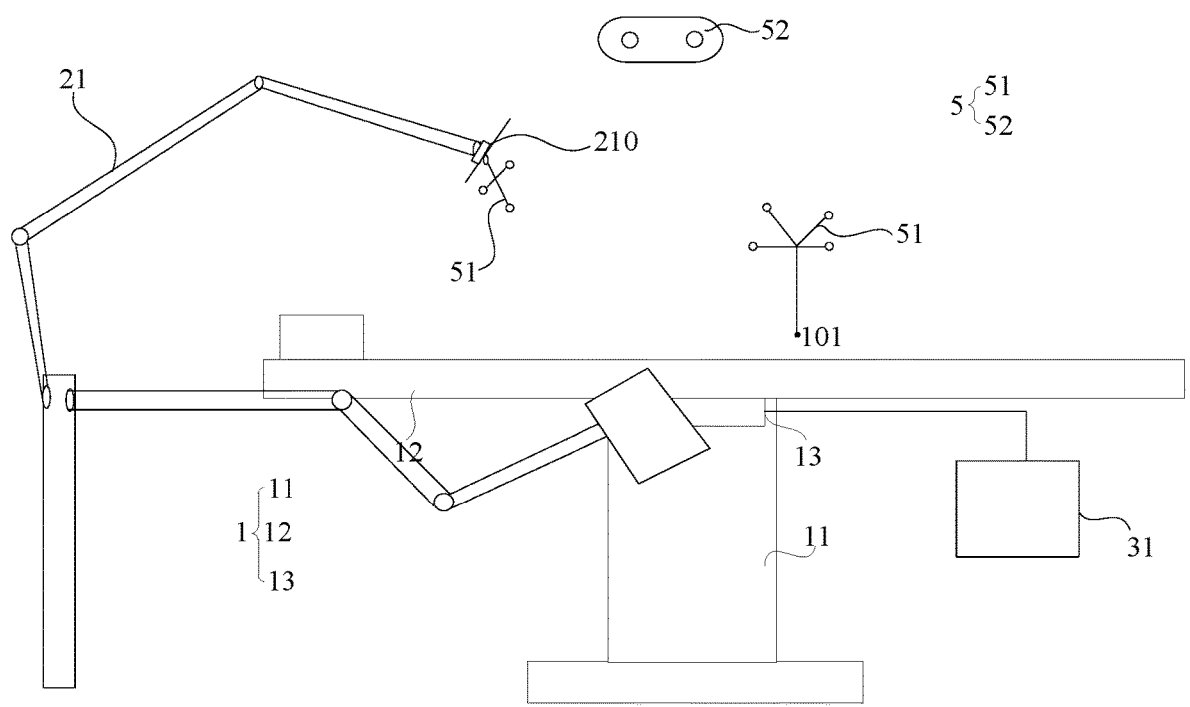
FIG. 6 is a structural diagram of another surgical operation monitoring system provided by an embodiment of the disclosure.

In some embodiments, as shown in FIGS. 3 and 6, the positioning and navigation device 5 may comprise positioning marks 51 and a tracking device 52. The positioning marks 51 can be arranged at the surgical site 101 and the actuating end 210 of the mechanical arm 21, and the tracking device 52 can track optical marks or non-optical marks arranged on the surgical site 101 and the actuating end 210 of the mechanical arm 21, such as radio frequency marks, magnetic marks, etc.

In this embodiment, by arranging the positioning marks 51 on the surgical site 101 and the actuating end 210 of the mechanical arm 21, the surgical site 101 and the actuating end 210 of the mechanical arm 21 can be tracked in real time in surgery, so that positioning accuracy can be improved.

For convenience of explanation, in the following description, it is assumed that the tracking device 52 tracks the optical marks arranged at the surgical site 101 and the actuating end 210 of the mechanical arm 21.

The optical mark may comprise an infrared reflector which can reflect infrared light. In this case, the tracking device 52 may comprise an infrared light source and an infrared camera. By arranging the optical marks at the actuating end 210 of the mechanical arm 21 and the surgical site 101, different patterns are formed by the infrared reflectors of the optical marks, so that the tracking device 52 can distinguish the optical marks and track the position and direction of the optical marks. For example, in the case of cutting the femur and tibia around the knee before changing the knee joint, optical markers may be provided on the femur, the tibia and the actuating end 210 of the mechanical arm 21, so that the tracking device 52 can track the femur, the tibia and the actuating end 210 of the mechanical arm 21.

For example, as shown in FIGS. 3 and 6, each optical mark can comprise a plurality of small spheres, and each small sphere is an infrared reflector. By arranging the plurality of small spheres into different patterns, the optical mark can emit infrared light with different patterns. In this way, the positions of the surgical site 101 and the actuating end 210 of the mechanical arm 21 in space can be acquired more accurately.

Further, the infrared camera can be a binocular camera, so as to acquire a three-dimensional image of a tracked object, and by establishing a navigation coordinate system for the acquired three-dimensional image, the coordinates of each optical mark in the navigation coordinate system can be acquired, so that the coordinates of the surgical site 101 and the actuating end 210 of the mechanical arm 21 in the navigation coordinate system can be acquired.

In some embodiments, the driver 13 can drive the support body 12 to tilt relative to the horizontal plane, and the driver 13 can be rotationally connected with the support body 12. In this case, the surgical operation monitoring system can also comprise a position sensor rigidly connected with a shaft of a motor in the driver 13, and a tilt angle of the support body 12 can be known by measuring a position of the shaft of the motor through the position sensor, so that the position of the support body 12 in three-dimensional space can be accurately obtained.

The position sensor 6 can be a position encoder, for example, a device that when a photosensitive element is used as an information acquisition component in the encoder, a transparent area and an opaque area are used to indicate a state of a code as "1" or "0", and through binary coding of "1" or "0", an acquired physical signal is converted into an electrical signal readable by a machine code for communication, transmission and storage.

Figure 9:
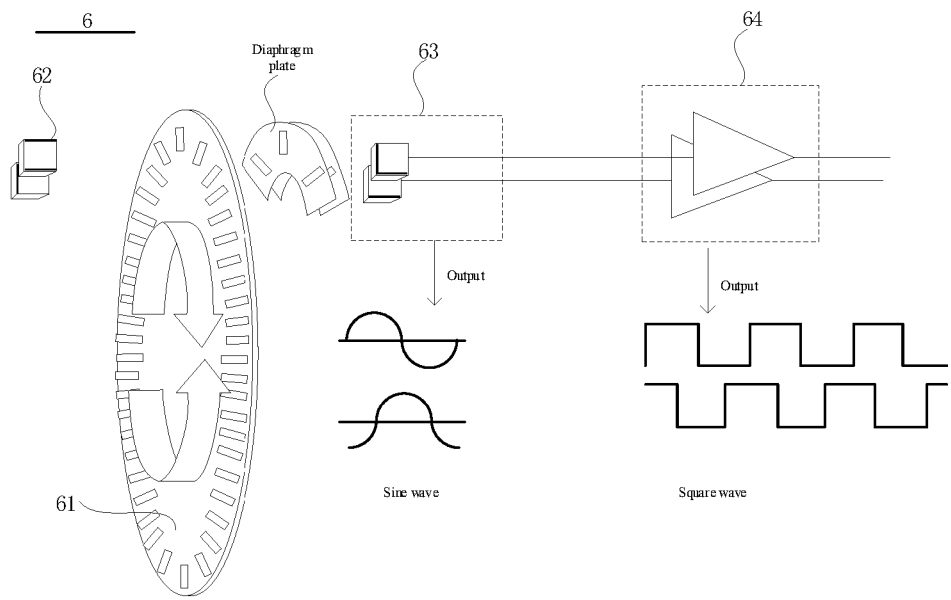
FIG. 9 is a structural diagram of a position sensor provided by an embodiment of the disclosure.

Hereinafter, the position encoder is assumed to be a photoelectric encoder. As shown in FIG. 9, the position encoder may comprise a code wheel 61, a light emitting source 62 and a receiver 63 arranged on opposite sides of the code wheel 61, and an amplifying and shaping circuit 64 electrically connected with the receiver 63. The code wheel 61 has many tiny slits (for example, 1024 slits, which is equivalent to subdividing a 360-degree circumference into many equal parts, such as 1024 groups, so that the angle difference between groups is $360/1024$ degrees, that is 0.3515625 degrees). During operation, when the code wheel 61 is driven to rotate, light will pass through the slits, the receiver 63 will instantly receive light pulses, which will be processed by the amplifying and shaping circuit 64, and then an electrical pulse signal is output. In this way, when the code wheel 61 rotates a circle, 1024 pulses will be output correspondingly. If a first pulse position is 0, then a second pulse position is 0.3515625°, a third pulse position is 0.3515625°*2, and so on. In this way, as long as there is an instrument which can read the number of the pulses, a corresponding position of the code wheel 61 can be known. Based on this, by applying the position encoder to the surgical robot system, surgical accuracy can be improved.

In this case, in order to prevent the surgical object 100 from being displaced due to the inclination of the support body 12, a guard fence may be provided on the support body 12.

Figure 7:
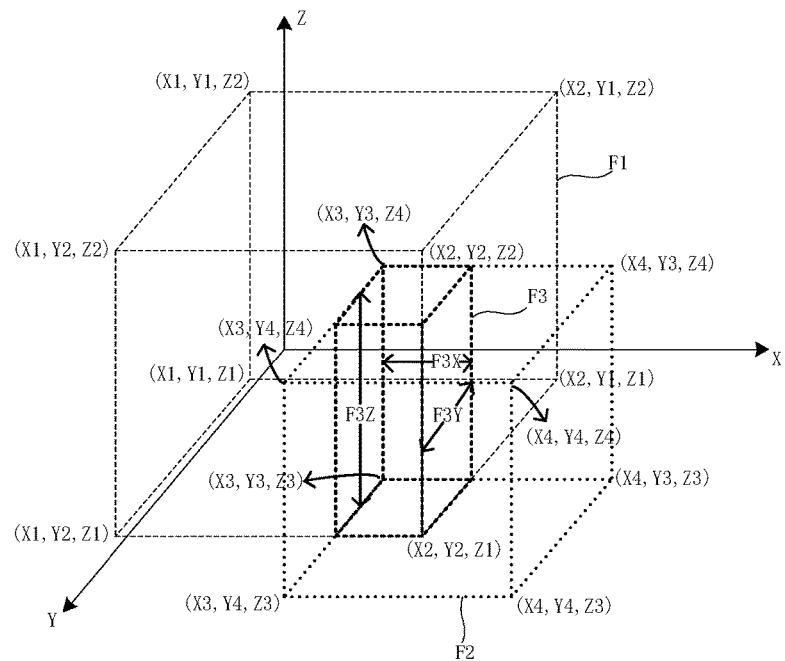
FIG. 7 is a schematic diagram showing that a moving range of an actuating end of a mechanical arm and an allowable moving range of a surgical site have an overlapping range according to an embodiment of the disclosure.

In some embodiments, as shown in FIGS. 5 and 7, the number of the drivers 13 is at least three, and the at least three drivers 13 include a first driver, a second driver and a third driver. The first driver is configured to drive the support body 12 to move in a first direction (X direction as shown in FIG. 7), the second driver is configured to drive the support body 12 to move in a second direction (Y direction as shown in FIG. 7), and the third driver is configured to drive the support body 12 to move in a third direction (Z direction as shown in FIG. 7), wherein the first direction X, the second direction Y and the third direction Z are perpendicular to each other.

Figure 8:
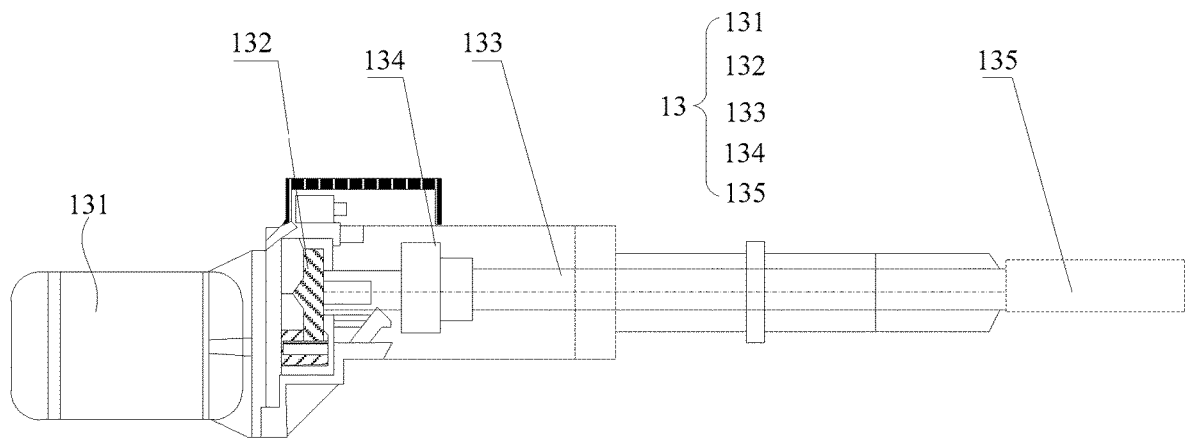
FIG. 8 is a structural diagram of a driver provided by an embodiment of the disclosure.

As shown in FIGS. 7 and 8, each driver 13 can be an electric push rod, comprising a motor 131, a reduction gear 132, a screw rod 133, a nut 134, a push rod 135, etc., wherein the push rod 135 is connected with the support body. During operation, the motor 131 rotates, and after being decelerated by the reduction gear 132, drives the screw rod 133 to rotate, thus driving the nut 134 to reciprocate linearly; in this way, the reciprocating motion of the push rod 135 is completed by the forward and reverse rotation of the motor 131, and then the linear reciprocating motion of the support body along the first direction X, the second direction Y and the third direction Z is realized.

In some embodiments, as shown in FIG. 9, the surgical operation monitoring system further comprises at least three position sensors 6, and the at least three position sensors 6 are a first position sensor, a second position sensor and a third position sensor which are electrically connected with the processor 31. The first position sensor is configured to detect a first deviation distance of the support body relative to a reference position in the first direction, the second position sensor is configured to detect a second deviation distance of the support body relative to the reference position in the second direction, and the third position sensor is configured to detect a third deviation distance of the support body relative to the reference position in the third direction.

The position sensor 6 may also be the position encoder as described above, so that the position of the support body 12 in the first direction X, the second direction Y and the third direction Z can be accurately acquired.

The reference position may be the position of the support body 12 when the motor 131 does not rotate forward, or the position of the support body 12 after the motor 131 rotates one or more circles forward, which is not limited here.

Let's take the motor in the first driver as an example. Assuming that the support body 12 moves to the right in the first direction X when the motor in the first driver rotates forward, then the first deviation distance DF refers to a distance that the support body 12 has shifted in the first direction X relative to the reference position. Because the first direction X includes a left direction and a right direction, the first deviation distance DF may be positive or negative. When the first deviation distance DF is positive, it is indicated that the support body 12 has moved |DF| to the right relative to the reference position, and when the first deviation distance is negative, it is indicated that the support body 12 has moved |DF| to the left relative to the reference position.

In this case, assuming that at the reference position, a total deviation distance of the support body 12 moving to the left in the first direction X is DLx, a total deviation distance of the support body moving to the right in the first direction X is DRx, and at the first moment, the first deviation distance of the support body 12 relative to the reference position is DF, then at the first moment, an allowable deviation distance $\Delta XL$ of the surgical site 101 moving to the left in the first direction X relative to the reference position is equal to DLx+DF, and an allowable deviation distance $\Delta XR$ of the surgical site moving to the right in the first direction x relative to the reference position is equal to DLx-DF.

On this basis, assuming that the coordinates of the surgical site 101 in the first direction X are XA, then the allowable moving range F2 of the surgical site 101 in the first direction X is a range defined by coordinates X3 obtained by subtracting the allowable deviation distance $\Delta XL$ of the surgical site 101 moving to the left in the first direction X relative to the reference position at the first moment from the coordinates XA of the surgical site 101 in the first direction X, and coordinates X4 obtained by adding the coordinates XA of the surgical site 101 in the first direction X to the allowable deviation distance $\Delta XR$ of the surgical site 101 moving to the right in the first direction X relative to the reference position at the first moment.

Similar to the first direction X, the allowable moving range F2 of the surgical site 101 in the second direction Y and the allowable moving range F2 of the surgical site 101 in the third direction Z can be obtained by the above calculation method, so as to obtain the allowable moving range F2 of the surgical site 101 in the whole coordinate system.

On this basis, when the positions of the surgical site 101 and the actuating end 210 of the mechanical arm 21 are acquired by the navigation and positioning device 5 described above, so that the processor 31 acquires the coordinates of the surgical site 101 and the actuating end 210 of the mechanical arm 21 in the world coordinate system, as shown in FIGS. 6 and 7, the moving range F1 of the actuating end 210 of the mechanical arm 21 may include a range defined from X1 to X2 in the first direction, a range defined from Y1 to Y2 in the second direction, and a range defined from Z1 to Z2 in the third direction. The allowable moving range F2 of the surgical site 101 described above may include a range defined from X3 to X4 in the first direction, a range defined from Y3 to Y4 in the second direction, and a range defined from Z3 to Z4 in the vertical direction.

On this basis, the overlapping range F3 refers to a spatial range defined by a first range F3X, a second range F3Y and a third range F3Z. The first range F3X is an overlapping range between the range defined from X1 to X2 and the range defined from X3 to X4, the second range F3Y is an overlapping range between the range defined from Y1 to Y2 and the range defined from Y3 to Y4, and the third range F3Z is an overlapping range between the range defined from Z1 to Z2 and the range defined from Z3 to Z4.

In some embodiments, under the condition that the allowable moving range F2 of the surgical site 101 at the first moment and the moving range F1 of the actuating end 210 of the mechanical arm 21 have an overlapping range F3, there are various implementation modes according to the different positions of X1, X2, X3 and X4, Y1, Y2, Y3 and Y4, and Z1, Z2, Z3 and Z4 in the coordinate system.

The following will take, as an example, the overlapping range F3X in the first direction X between the allowable moving range F2 of the surgical site 101 at the first moment and the moving range F2 of the actuating end 210 of the mechanical arm 21.

It can be understood by those skilled in the art that the second direction and the third direction are similar to the first direction, and may also have various second ranges F3Y and third ranges F3Z, and the range jointly defined by the first range F3X, the second range F3Y and the third range F3Z is the overlapping range F3.

Figure 10:
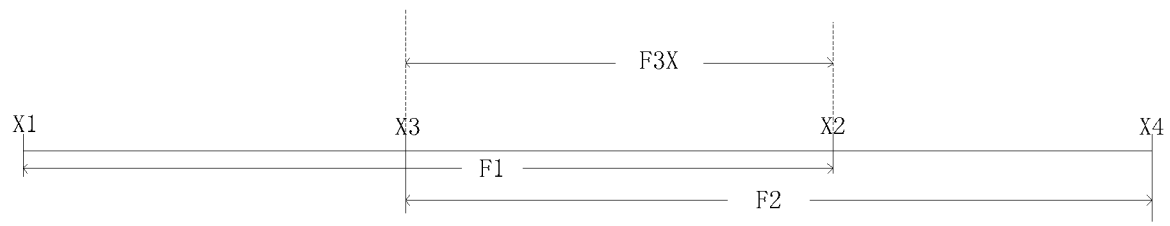
FIG. 10 is a structural diagram of an overlapping range between a moving range of an actuating end of a mechanical arm and an allowable moving range of a surgical site in a first direction according to an embodiment of the disclosure.

In a first implementation mode, as shown in FIG. 10, the coordinates of X1 are smaller than those of X3, the coordinates of X2 are larger than those of X3, and the coordinates of X4 are larger than those of X2. In this case, the first range F3X is a range defined by X3 to X2. In this implementation mode, the surgical site can only move to the range defined by X3 to X2 under the driving of the support body 12.

Figure 11:
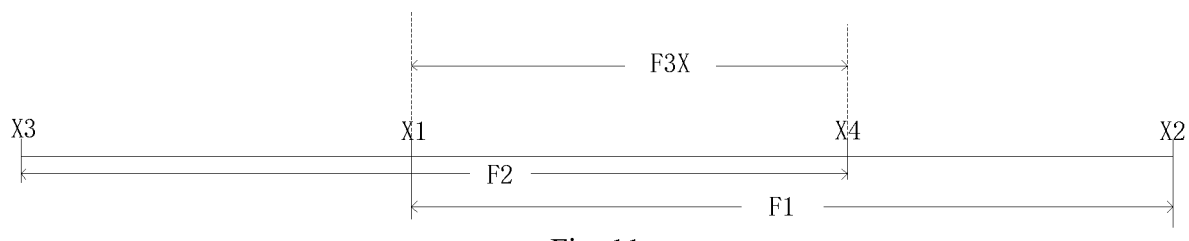
FIG. 11 is a structural diagram of another overlapping range between a moving range of an actuating end of a mechanical arm and an allowable moving range of a surgical site in a first direction according to an embodiment of the disclosure.

In a second implementation mode, as shown in FIG. 11, the coordinates of X3 are smaller than those of X1, the coordinates of X4 are larger than those of X1, and the coordinates of X2 are larger than those of X4. In this case, the first range F3X is a range defined by X1 to X4.

In this implementation mode, the surgical site can only move to the range defined by X1 to X4 under the driving of the support body 12.

Figure 12:
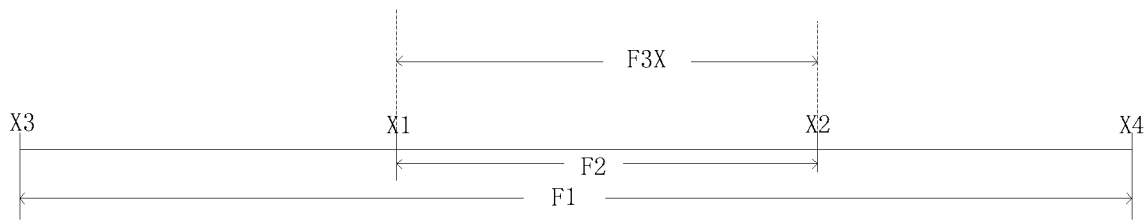
FIG. 12 is a structural diagram of another overlapping range between a moving range of an actuating end of a mechanical arm and an allowable moving range of a surgical site in a first direction according to an embodiment of the disclosure.

In a third implementation mode, as shown in FIG. 12, the coordinates of X3 are smaller than those of X1, the coordinates of X2 are larger than those of X1, and the coordinates of X4 are larger than those of X2. In this case, the first range F3X is a range defined by X1 to X2. In this implementation mode, the surgical site can only move to the range defined by X1 to X2 under the driving of the support body 12.

Figure 13:
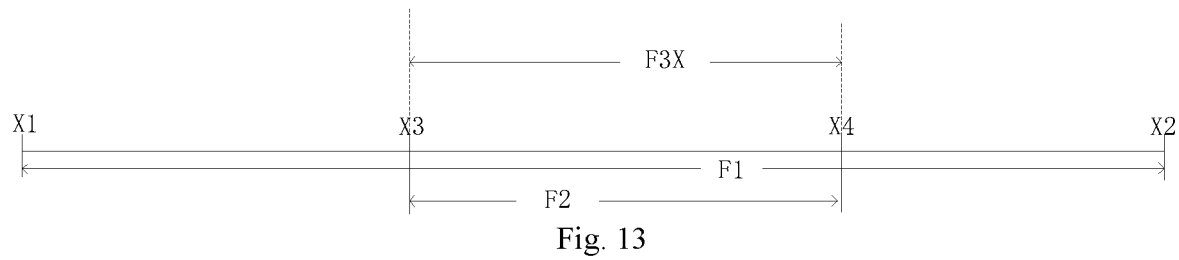
FIG. 13 is a structural diagram of another overlapping range between a moving range of an actuating end of a mechanical arm and an allowable moving range of a surgical site in a first direction according to an embodiment of the disclosure.

In a fourth implementation mode, as shown in FIG. 13, the coordinates of X1 are smaller than those of X3, the coordinates of X4 are larger than those of X3, and the coordinates of X2 are larger than those of X4. In this case, the first range F3X is a range defined by X3 to X4.

In this implementation mode, the surgical site can only move to the range defined by X3 to X4 under the driving of the support body 12.

In order to more clearly explain the overlapping range F3 between the allowable moving range F2 of the surgical site at the first moment and the moving range F2 of the actuating end of the mechanical arm, FIG. 7 shows an example of overlapping ranges between the allowable moving range F2 of the surgical site at the first moment and the moving range F2 of the actuating end of the mechanical arm in the first direction X, the second direction Y and the third direction Z.

It can be known from FIG. 7 that by representing the vertices of the allowable moving range F2 of the surgical site at the first moment and the moving range F1 of the actuating end of the mechanical arm by coordinates, the range defined from X1 to X2 can be expressed as [X1, X2], (X1, X2), [X1, X2) or (X1, X2], the range defined from Y1 to Y2 can be expressed as [Y1, Y2], (Y1, Y2), [Y1, Y2) or (Y1, Y2], the range defined from Z1 to Z2 can be expressed as [Z1, Z2], (Z1, Z2), [Z1, Z2) or (Z1, Z2], the range from X3 to X4 can be expressed as [X3, X4], (X3, X4), [X3, X4) or (X3, X4], the range defined from Y3 to Y4 can be expressed as [Y3, Y4], (Y3, Y4), [Y3, Y4) or (Y3, Y4], and the range defined from Z3 to Z4 can be expressed as [Z3, Z4], (Z3, Z4), [Z3, Z4) or (Z3, Z4].

Under the condition that the allowable moving range F2 of the surgical site at the first moment and the moving range F1 of the actuating end of the mechanical arm have an overlapping range F3, any point (X, Y, Z) located within the overlapping range F3 must satisfy that X, Y and Z are all within the overlapping ranges of their respective directions (such as the first range F3X, the second range F3Y and the third range F3Z).

By way of example, as shown in FIG. 7, still assuming that in the first direction X, the coordinates of X1 are smaller than those of X3, the coordinates of X2 are larger than those of X3, the coordinates of X4 are larger than those of X2, and the overlapping range in the first direction X (the first range F3X) is the range defined by X3 to X2; in the second direction Y, the coordinates of Y1 are smaller than those of Y3, the coordinates of Y2 are larger than those of Y3, the coordinates of Y4 are larger than those of Y2, and the overlapping range in the second direction Y (the second range F3Y) is the range defined by Y3 to Y2; and in the third direction Z, the coordinates of Z1 are smaller than those of Z3, the coordinates of Z2 are larger than those of Z3, the coordinates of Z4 are larger than those of Z2, and the overlapping range in the third direction Z (the third range F3Z) is the range defined by Z3 to Z2, the overlapping range F3 refers to a range corresponding to all coordinate points where a value of X is within the range defined by X3 to X2, a value of Y is within the range defined by Y3 to Y2, and a value of Z is within the range defined by Z3 to Z2.

Further, it should be noted that the above description is only made by assuming that the coordinates of X1 are smaller than those of X2, the coordinates of X3 are smaller than those of X4, the coordinates of Y1 are smaller than those of Y2, the coordinates of Y3 are smaller than those of Y4, the coordinates of Z1 are smaller than those of Z2, and the coordinates of Z3 are smaller than those of Z4. Those skilled in the art can understand that in practical applications, the coordinates of X1 can be larger than those of X2, and the coordinates of X3 can also be larger than those of X4; similarly, the coordinates of Y1 can be larger than those of Y2, the coordinates of Y3 can also be larger than those of Y4, the coordinates of Z1 can be larger than those of Z2, and the coordinates of Z3 can also be larger than those of Z4. The protection scope of this disclosure is not limited here.

An embodiment of the disclosure provides a surgical operation monitoring system. According to the surgical operation monitoring system, the positions of the actuating end 210 of the mechanical arm 21 of the surgical robot 2 and the surgical site 101 of the surgical object 100 are detected by using an optical positioning device 4 in the surgical process, and when the surgical object 100 is displaced so that the surgical site 101 exceeds the moving range F1 of the actuating end 210 of the mechanical arm 21, the allowable moving range F2 of the surgical site 101 at the first moment can be obtained by the interaction between the position sensor 6 arranged on the support body 12 and the processor 31; and under the condition that the allowable moving range F2 of the surgical site 101 at the first moment and the moving range F1 of the actuating end 210 of the mechanical arm 21 have the overlapping range F3, the support body 12 is controlled to drive the surgical site 101 to move into the overlapping range F3. In this way, the position deviation of the surgical site 101 can be compensated, the position deviation caused by the posture change of the surgical object 100 in the surgical process can be reduced, the requirement for the spatial moving range of the surgical robot 2 can be effectively reduced, automatic control can be realized without manual adjustment, and the system is especially suitable for the situation that the position and posture cannot be easily adjusted by the surgical robot 2.

In some embodiments, the processor 31 is further configured to control the actuating end 210 of the mechanical arm 21 to move to a position corresponding to the position of the surgical site 101 at the first moment when the position of the surgical site 101 at the first moment does not exceed the moving range F1 of the actuating end 210 of the mechanical arm 21 and the surgical site 101 deviates from the actuating end 210 of the mechanical arm 21 at the first moment.

Figure 14:
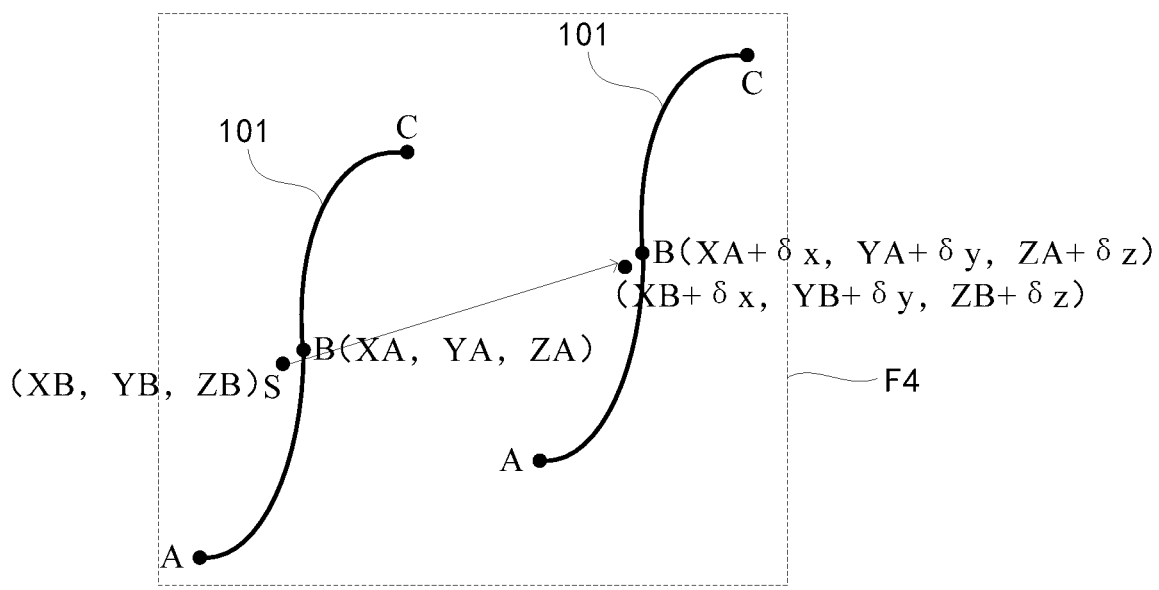
FIG. 14 is a schematic diagram of controlling a surgical site to move to a position corresponding to a position of the surgical site at a first moment when the surgical site does not exceed a moving range of an actuating end of a mechanical arm and the surgical site deviates from the actuating end of the mechanical arm at the first moment according to an embodiment of the disclosure.
Figure 14:
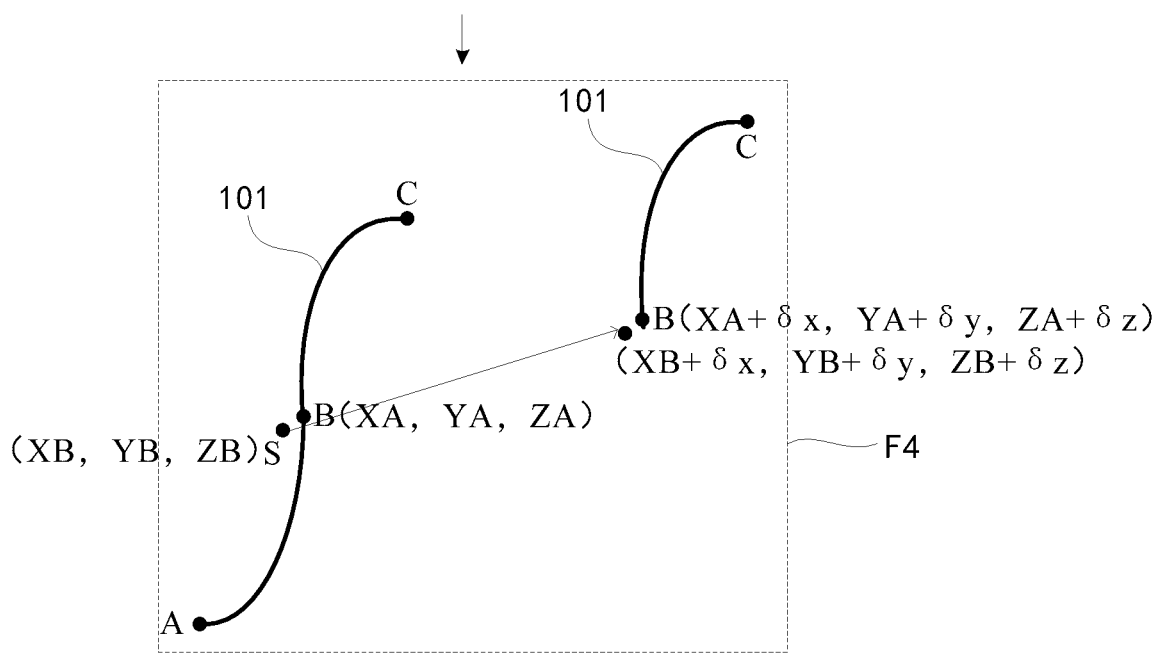
Figure 15:
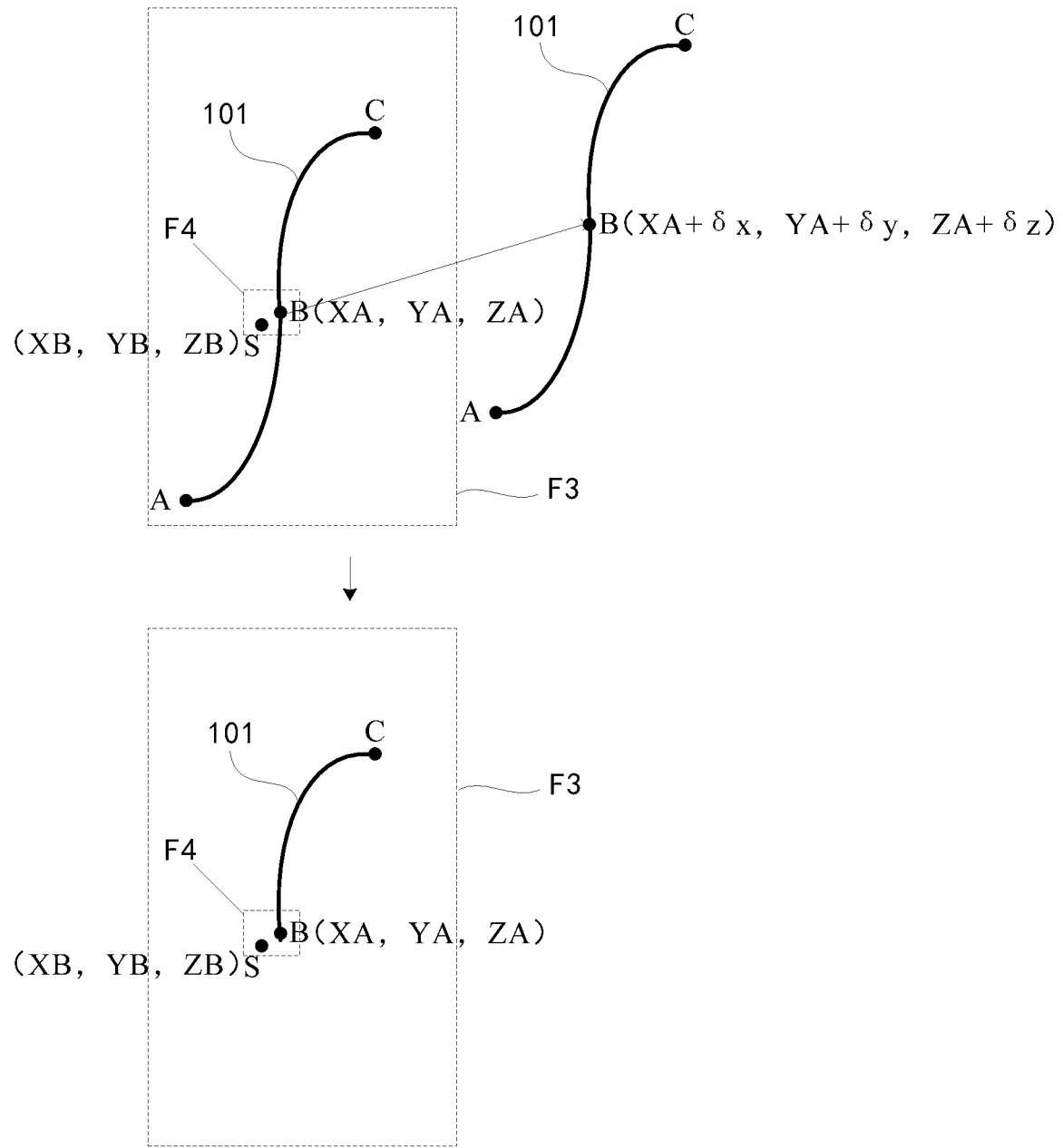
FIG. 15 is a schematic diagram of controlling a surgical site to move to a position corresponding to a position of the surgical site at a first moment when the surgical site exceeds a moving range of an actuating end of a mechanical arm and the actuating end of the mechanical arm is located within an overlapping range at the first moment according to an embodiment of the disclosure.

The expression that the surgical site 101 does not deviate from the actuating end 210 of the mechanical arm 21 at the first moment means that, as shown in FIG. 14, at the first moment, the deviation of the surgical site 101 from the actuating end 210 of the mechanical arm 21 is within an operable range F4, so that the actuating end 210 of the mechanical arm 21 can perform operation on the surgical site 101. On the contrary, the expression that the surgical site 101 deviates from the actuating end 210 of the mechanical arm 21 at the first moment means that, as shown in FIG. 15, at the first moment, the deviation of the surgical site 101 from the actuating end 210 of the mechanical arm 21 is beyond the operable range F4, so that the actuating end 210 of the mechanical arm 21 cannot perform operation on the surgical site 101.

In this case, the position corresponding to the position of the surgical site 101 at the first moment refers to a position where the actuating end 210 of the mechanical arm 21 can perform operation on the surgical site 101 at the first moment. The deviation between the corresponding position and the position of the surgical site 101 at the first moment is within the operable range F4.

Here, assuming that the surgical site 101 is a curved wound as shown in FIG. 14, the position of the surgical site 101 at the first moment is a position indicated by point B of the curved wound before the surgical site 101 deviates from the actuating end 210 of the mechanical arm 21 at the first moment, and the position corresponding to the position of the surgical site 101 at the first moment is the position where the actuating end 210 of the mechanical arm 21 can perform operation on the surgical site 101, as indicated by point S; further assuming that at the first moment, before deviation occurs, the coordinates of the actuating end 210 of the mechanical arm 21 are (XB, YB, ZB), the coordinates of the position of the surgical site 101 at the first moment are (XA, YA, ZA), and the deviation of the surgical site 101 from the actuating end 210 of the mechanical arm 21 is ($\delta x$, $\delta y$, $\delta z$), that is to say, the deviation of the surgical site 101 from the actuating end 210 of the mechanical arm 21 is $\delta x$ in the first direction, $\delta y$ in the second direction and $\delta z$ in the third direction, where $\delta x$, $\delta y$ and $\delta z$ may be positive or negative; and taking the first direction as an example, in the coordinate system, if the surgical site 101 deviates to the left from the actuating end 210 of the mechanical arm 21, $\delta x$ is negative, and if the surgical site deviates to the right, $\delta x$ is positive.

In this case, the coordinates of the surgical site after the surgical site 101 deviates from the actuating end 210 of the mechanical arm 21 can be marked as (XA+$\delta x$, YA+$\delta y$, ZA+$\delta z$). At this point, moving the actuating end 210 of the mechanical arm 21 to the position corresponding to the position of the surgical site 101 at the first moment means moving the actuating end 210 of the mechanical arm 21 to a position with the coordinates (XB+$\delta x$, YB+$\delta y$, ZB+$\delta z$).

In these embodiments, by controlling the actuating end 210 of the mechanical arm 21 to move to the position corresponding to the position of the surgical site 101 at the first moment when the position of the surgical site 101 at the first moment does not exceed the moving range F1 of the actuating end 210 of the mechanical arm 21 and the surgical site 101 deviates from the actuating end 210 of the mechanical arm 21 at the first moment, the actuating end 210 of the mechanical arm 21 can follow the surgical site 101, thus avoiding accidental injuries caused by the displacement of the surgical site 101 and improving surgical accuracy.

In some embodiments, the processor 31 is further configured to control the actuating end 210 of the mechanical arm 21 to perform operation according to a first surgical path when the position of the surgical site 101 at the first moment does not exceed the moving range F1 of the actuating end 210 of the mechanical arm 21 and the surgical site 101 does not deviate from the actuating end 210 of the mechanical arm 21 at the first moment, correct the first surgical path according to the position corresponding to the position of the surgical site 101 at the first moment to obtain a second surgical path when the position of the surgical site 101 at the first moment does not exceed the moving range F1 of the actuating end 210 of the mechanical arm 21 and the surgical site 101 deviates from the actuating end 210 of the mechanical arm 21 at the first moment, and control the actuating end 210 of the mechanical arm 21 to perform operation according to the second surgical path after the actuating end 210 of the mechanical arm 21 moves to the position corresponding to the position of the surgical site 101 at the first moment.

In these embodiments, the first surgical path may be a preset path. That is to say, before surgery, an attending doctor plans the surgical path according to the surgical site 101 and stores it in the processor 31, and in surgery, the doctor only needs to control the actuating end 210 of the mechanical arm 21 to perform operation according to the stored surgical path.

Here, assuming that the first surgical path is a movement path by which the actuating end 210 of the mechanical arm 21 drives a driller to sew the curved wound as shown in FIG. 14, and the first surgical path can be a path starting from point A of the wound and moving from A to C along the extension direction of the wound.

In the surgical process, if the position of the surgical site 101 at the first moment does not exceed the moving range F1 of the actuating end 210 of the mechanical arm 21, the surgical site 101 deviates from the actuating end 210 of the mechanical arm 21 at the first moment, the previous path (first surgical path) cannot be used for surgical operation, that is, the deviation of the surgical site 101 from the actuating end 210 of the mechanical arm 21 exceeds the operable range F4, still assuming that the position of the surgical site 101 at the first moment is the position indicated by point B of the curved wound before the deviation occurs, the position corresponding to the position of the surgical site 101 at the first moment is the position where the actuating end 210 of the mechanical arm 21 can perform operation on the surgical site 101, such as the position indicated by point S, and the coordinates after the surgical site 101 deviates from the actuating end 210 of the mechanical arm 21 are (XA+$\delta x$, YA+$\delta y$, Za+$\delta z$), then moving the actuating end 210 of the mechanical arm 21 to the position corresponding to the position of the surgical site 101 at the first moment means moving the actuating end 210 of the mechanical arm 21 to the position with the coordinates (XB+$\delta x$, Yb+$\delta y$, ZB+$\delta z$).

In this case, correcting the first surgical path according to the position corresponding to the position of the surgical site 101 at the first moment may comprise:

taking the current position, that is, the position of the surgical site 101 at the first moment (the position indicated by point B of the curved wound described above) as a starting point (coordinates are (Xa+δx, Ya+δy, ZA+δz)), and controlling the actuating end 210 of the mechanical arm 21 to continue the operation according to a path parallel to the first surgical path, so as to correct the first surgical path, wherein a movement path of the actuating end 210 of the mechanical arm 21 from the starting point is the second surgical path (that is, a surgical path corresponding to point B to point C as shown in FIG. 14).

In yet other embodiments, the processor is further configured to acquire the position of the actuating end 210 of the mechanical arm 21 at the first moment, and control the driver 13 to drive the support body 12 to move to make the support body 12 drive the surgical site 101 to move into the overlapping range F3 when the position of the surgical site 101 at the first moment exceeds the moving range F1 of the actuating end 210 of the mechanical arm 21 and the position of the actuating end 210 of the mechanical arm 21 at the first moment is within the overlapping range F3, including controlling the driver 13 to drive the support body 12 to move, so that the support body 12 drives the surgical site 101 to move to a position corresponding to the position of the actuating end 210 of the mechanical arm 21 at the first moment.

In this embodiment, the processor 31 can also obtain the position of the actuating end 210 of the mechanical arm 21 at the first moment through the positioning and navigation device 5, for example, the coordinates (XB, YB, ZB) of the actuating end 210 of the mechanical arm 21 in the world coordinate system at the first moment can be obtained. Still assuming that the overlapping range F3 is the range corresponding to all coordinate points within the range where the value of X is within the range defined by X3 to X2, the value of Y is within the range defined by Y3 to Y2, and the value of Z is within the range defined by Z3 to Z2, then X3<XB<X2, Y3<YB<Y2, and Z3<ZB<Z2.

The position corresponding to the position of the actuating end 210 of the mechanical arm 21 at the first moment refers to the position where the actuating end 210 of the mechanical arm 21 can perform operation on the surgical site 101 at the first moment. The deviation between the corresponding position and the position of the surgical site 101 at the first moment is within the operable range F4.

Here, still assuming that the surgical site 101 is a curved wound as shown in FIG. 15, the position of the surgical site 101 at the first moment is a position indicated by point B of the curved wound before the surgical site 101 deviates from the actuating end 210 of the mechanical arm 21 at the first moment, and the position corresponding to the position of the surgical site 101 at the first moment is the position where the actuating end 210 of the mechanical arm 21 can perform operation on the surgical site 101, as indicated by point S; further assuming that at the first moment, before deviation occurs, the coordinates of the actuating end 210 of the mechanical arm 21 are (XB, YB, ZB), the coordinates of the position of the surgical site 101 at the first moment are (XA, YA, ZA), and the deviation of the surgical site 101 from the actuating end 210 of the mechanical arm 21 is (δx, δy, δz), that is to say, the deviation of the surgical site 101 from the actuating end 210 of the mechanical arm 21 is δx in the first direction, δy in the second direction and δz in the third direction, where δx, δy and δz may be positive or negative; and taking the first direction as an example, in the coordinate system, if the surgical site 101 deviates to the left from the actuating end 210 of the mechanical arm 21, δx is negative, and if the surgical site deviates to the right, δx is positive.

In this case, the coordinates of the surgical site after the surgical site 101 deviates from the actuating end 210 of the mechanical arm 21 can be marked as (XA+δx, YA+δy, ZA+δz). At this point, controlling the driver 13 to drive the support body 12 to move, so that the support body 12 drives the surgical site 101 to move to the position corresponding to the position of the actuating end 210 of the mechanical arm 21 at the first moment means controlling the driver 13 to drive the support body 12 to move so that the support body 12 drives the surgical site 101 to move to a position with the coordinates (XA, YA, ZA).

In these embodiments, by controlling the driver 13 to drive the support body 12 to move so that the support body 12 drives the surgical site 101 to move to the position corresponding to the position of the actuating end 210 of the mechanical arm 21 at the first moment, the actuating end 210 of the mechanical arm 21 can follow the surgical site 101, thus avoiding accidental injuries caused by the displacement of the surgical site 101 and improving surgical accuracy.

Figure 16:
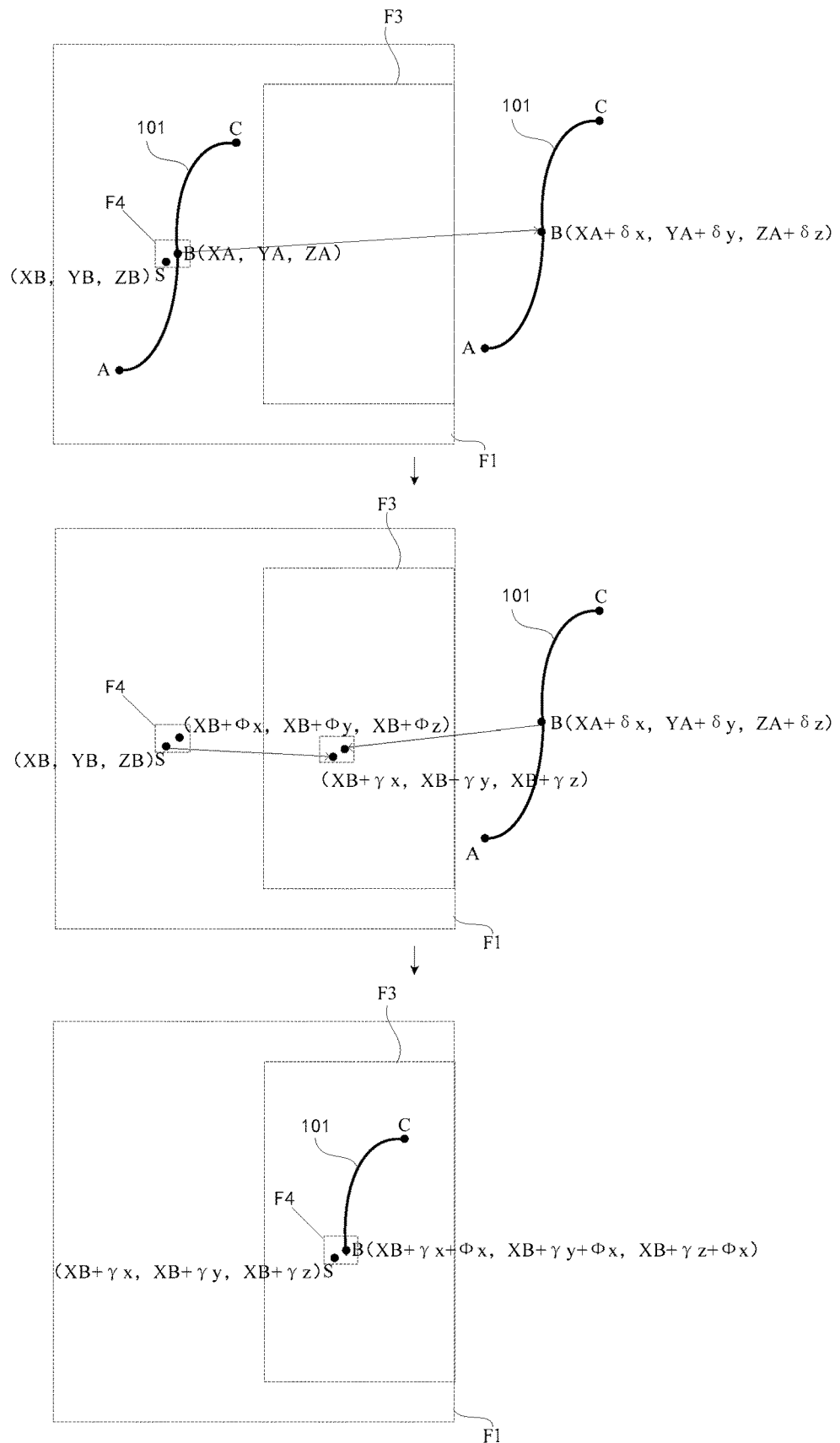
FIG. 16 is a schematic diagram of controlling an actuating end of a mechanical arm to move to a first position of an overlapping range and controlling a surgical site to move to a second position when the surgical site exceeds a moving range of the actuating end of the mechanical arm and the actuating end of the mechanical arm is located beyond the overlapping range at a first moment according to an embodiment of the disclosure.

In other embodiments, as shown in FIG. 16, the processor is further configured to control the actuating end 210 of the mechanical arm 21 to move to a first position within the overlapping range F3 when the position of the actuating end of the mechanical arm at the first moment is beyond the overlapping range F3, and is specifically configured to control the driver 13 to drive the support body 12 to move, so that the support body 12 drives the surgical site 101 to move to a second position within the overlapping range F3, and the second position is a position corresponding to the first position.

Similar to the above embodiments, the processor 31 can also obtain the position of the actuating end 210 of the mechanical arm 21 at the first moment through the positioning and navigation device 5. Assuming that the coordinates of the actuating end 210 of the mechanical arm 21 in the world coordinate system at the first moment are (XB, YB, ZB), and the overlapping range F3 is the range corresponding to all coordinate points within the range where the value of X is within the range defined by X3 to X1, the value of Y is within the range defined by Y3 to Y1, and the value of Z is within the range defined by Z3 to Z2, then XB<X1 or X3<XB, YB<Y1 or X3<YB, or ZB<Z1 or Z3<ZB.

The second position is a position corresponding to the first position, which means that when the actuating end 210 of the mechanical arm 21 is in the first position, the second position is a position where the actuating end 210 of the mechanical arm 21 can perform surgical operation on the surgical site 101. At this corresponding position, the offset of the surgical site 101 relative to the actuating end 210 of the mechanical arm 21 is within the operable range F4.

Here, still assuming that the surgical site 101 is a curved wound as shown in FIG. 16, the position of the surgical site 101 at the first moment is a position indicated by point B of the curved wound before the surgical site 101 deviates from the actuating end 210 of the mechanical arm 21 at the first moment, and the position corresponding to the position of the surgical site 101 at the first moment is the position where the actuating end 210 of the mechanical arm 21 can perform operation on the surgical site 101, as indicated by point S; further assuming that at the first moment, before deviation occurs, the coordinates of the actuating end 210 of the mechanical arm 21 are (XB, YB, ZB), the coordinates of the position of the surgical site 101 at the first moment are (XA, YA, ZA), and the deviation of the surgical site 101 from the actuating end 210 of the mechanical arm 21 is (δx, δy, δz), that is to say, the deviation of the surgical site 101 from the actuating end 210 of the mechanical arm 21 is δx in the first direction, δy in the second direction and δz in the third direction, where δx, δy and δz may be positive or negative; and taking the first direction as an example, in the coordinate system, if the surgical site 101 deviates to the left from the actuating end 210 of the mechanical arm 21, δx is negative, and if the surgical site deviates to the right, δx is positive.

In this case, the coordinates of the surgical site after the surgical site 101 deviates from the actuating end 210 of the mechanical arm 21 can be marked as (XA+δx, YA+δy, ZA+δz). At this point, assuming that the first position within the overlapping range F3 is the position where the actuating end 210 of the mechanical arm 21 deviates by (γx, γy, γz), where γx is the deviation in the first direction, γy is the deviation in the second direction, γz is the deviation in the third direction, and γx, γy and γz may be positive or negative, then controlling the actuating end 210 of the mechanical arm 21 to move to the first position within the overlapping range F3 means controlling the actuating end 210 of the mechanical arm 21 to move to a position with the coordinates (XB+γx, XB+γy, XB+γz). At this point, assuming that before the surgical site 101 deviates from the actuating end 210 of the mechanical arm 21, the coordinates of the surgical site 101 are the coordinates where the actuating end 210 of the mechanical arm 21 deviates by (Φx, Φy, Φz), where Φx is the deviation in the first direction, Φy is the deviation in the second direction, Φz is the deviation in the third direction, and Φx, Φy and Φz may be positive or negative, then the coordinates of the surgical site can be represented by (XB+Φx, XB+Φy, XB+Φz), and controlling the driver 13 to drive the support body 12 to move so that the support body 12 drives the surgical site 101 to the second position within the overlapping range F3 means controlling the driver 13 to drive the support body 12 to move so that the support body 12 drives the surgical site 101 to move to the position with the coordinates (XB+γx+Φx, XB+γy+Φx, XB+γz+Φx).

In these embodiments, by controlling the actuating end 210 of the mechanical arm 21 and the surgical site 101 to move into the overlapping range F3, and making the deviation of the actuating end 210 of the mechanical arm 21 and the surgical site 101 within the operable range F4, the position of the surgical site 101 can be compensated in time, thus avoiding accidental injuries caused by position deviation of the surgical site 101 and improving surgical accuracy.

In yet other embodiments, the processor 31 is further configured to control the actuating end 210 of the mechanical arm 21 to perform operation according to the first surgical path after the support body 12 drives the surgical site 101 to move to the position corresponding to the position of the actuating end 210 of the mechanical arm 21 at the first moment when the position of the actuating end 210 of the mechanical arm 21 is located within the overlapping range F3, correct the first surgical path according to a second position to obtain a third surgical path and control the actuating end 210 of the mechanical arm 21 to perform operation according to the third surgical path when the position of the actuating end 210 of the mechanical arm 21 at the first moment is beyond the overlapping range F3.

In these embodiments, the first surgical path may be a preset path. That is to say, before surgery, an attending doctor plans the surgical path according to the surgical site 101 and stores it in the processor 31, and in surgery, the doctor only needs to control the actuating end 210 of the mechanical arm 21 to perform operation according to the stored surgical path.

Here, assuming that the first surgical path is a movement path by which the actuating end 210 of the mechanical arm 21 drives a driller to sew the curved wound as shown in FIG. 15, and the first surgical path can be a path starting from point A of the wound and moving from A to C along the extension direction of the wound.

In the surgical process, if the surgical site 101 deviates from the actuating end 210 of the mechanical arm 21 at the first moment, the previous path (first surgical path) cannot be used for surgical operation, that is, the deviation of the surgical site 101 from the actuating end 210 of the mechanical arm 21 exceeds the operable range F4, still assuming that the position of the surgical site 101 at the first moment is the position indicated by point B of the curved wound before the deviation occurs, the position corresponding to the position of the surgical site 101 at the first moment is the position where the actuating end 210 of the mechanical arm 21 can perform operation on the surgical site 101, such as the position indicated by point S, and the coordinates after the surgical site 101 deviates from the actuating end 210 of the mechanical arm 21 are (XA+δx, YA+δy, Za+δz), then at this point, still assuming that the first position within the overlapping range F3 is the position where the actuating end 210 of the mechanical arm 21 deviates by (γx, γy, γz), and the coordinates of the surgical site 101 are the coordinates (Φx, Φy, Φz) of the deviation of the actuating end 210 of the mechanical arm 21 before the surgical site 101 deviates from the actuating end 210 of the mechanical arm 21, then controlling the actuating end 210 of the mechanical arm 21 to move to the first position within the overlapping range F3 means controlling the actuating end 210 of the mechanical arm 21 to move to a position with the coordinates (XB+γx, XB+γy, XB+γz), and controlling the driver 13 to drive the support body 12 to move so that the support body 12 drives the surgical site 101 to the second position within the overlapping range F3 means controlling the driver 13 to drive the support body 12 to move so that the support body 12 drives the surgical site 101 to move to the position with the coordinates (XB+γx+Φx, XB+γy+Φx, XB+γz+Φx).

In this case, correcting the first surgical path according to the second position may comprise:

taking the second position (the position indicated by point B of the curved wound described above) as a starting point (coordinates are (XB+γx+Φx, XB+γy+Φx, XB+γz+Φx)), and controlling the actuating end 210 of the mechanical arm 21 to continue the operation according to a path parallel to the first surgical path, so as to correct the first surgical path, wherein a movement path of the actuating end 210 of the mechanical arm 21 from the starting point is the third surgical path (that is, a surgical path corresponding to point B to point C).

In some embodiments, the surgical operation monitoring system further comprises an alarm, and the processor 31 is further configured to control the mechanical arm 21 to stop moving and control the alarm to give an alarm when the position of the surgical site 101 exceeds the moving range F1 of the actuating end 210 of the mechanical arm 21 and the allowable moving range F2 of the surgical site at the first moment and the moving range F1 of the actuating end 210 of the mechanical arm 21 do not have an overlapping range F3.

That is, the operation can be suspended at this point, and resumed by manually adjusting the position of the support body 12.

An embodiment of the disclosure provides a surgical operation monitoring method, which is applied to the above-mentioned surgical operation monitoring system. As shown in FIGS. 1 and 2, the surgical operation monitoring system comprises a surgical support device 1 and a surgical robot 2. The surgical support device 1 comprises a stand 11, a support body 12 mounted on the stand 11 and a driver 13 configured to drive the support body 12 to move relative to the stand 11, and the support body 12 is configured to support a surgical object 100. The surgical robot 2 comprises mechanical arms 21 with actuating ends 210.

Figure 17:
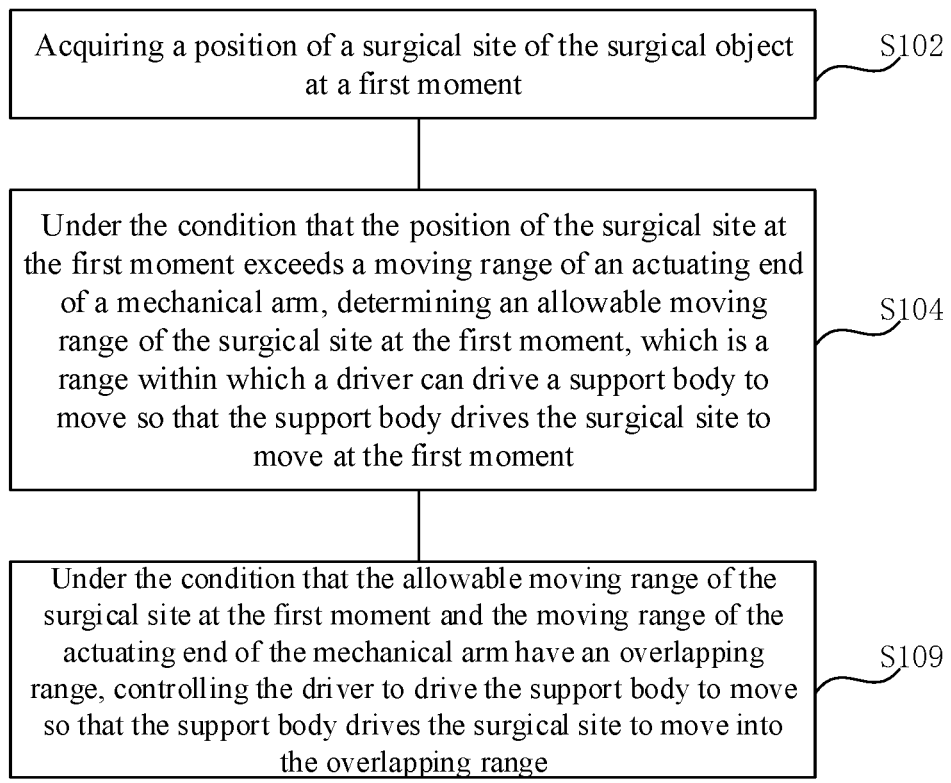
FIG. 17 is a flowchart of a surgical operation monitoring method provided by an embodiment of the disclosure.
Figure 18:
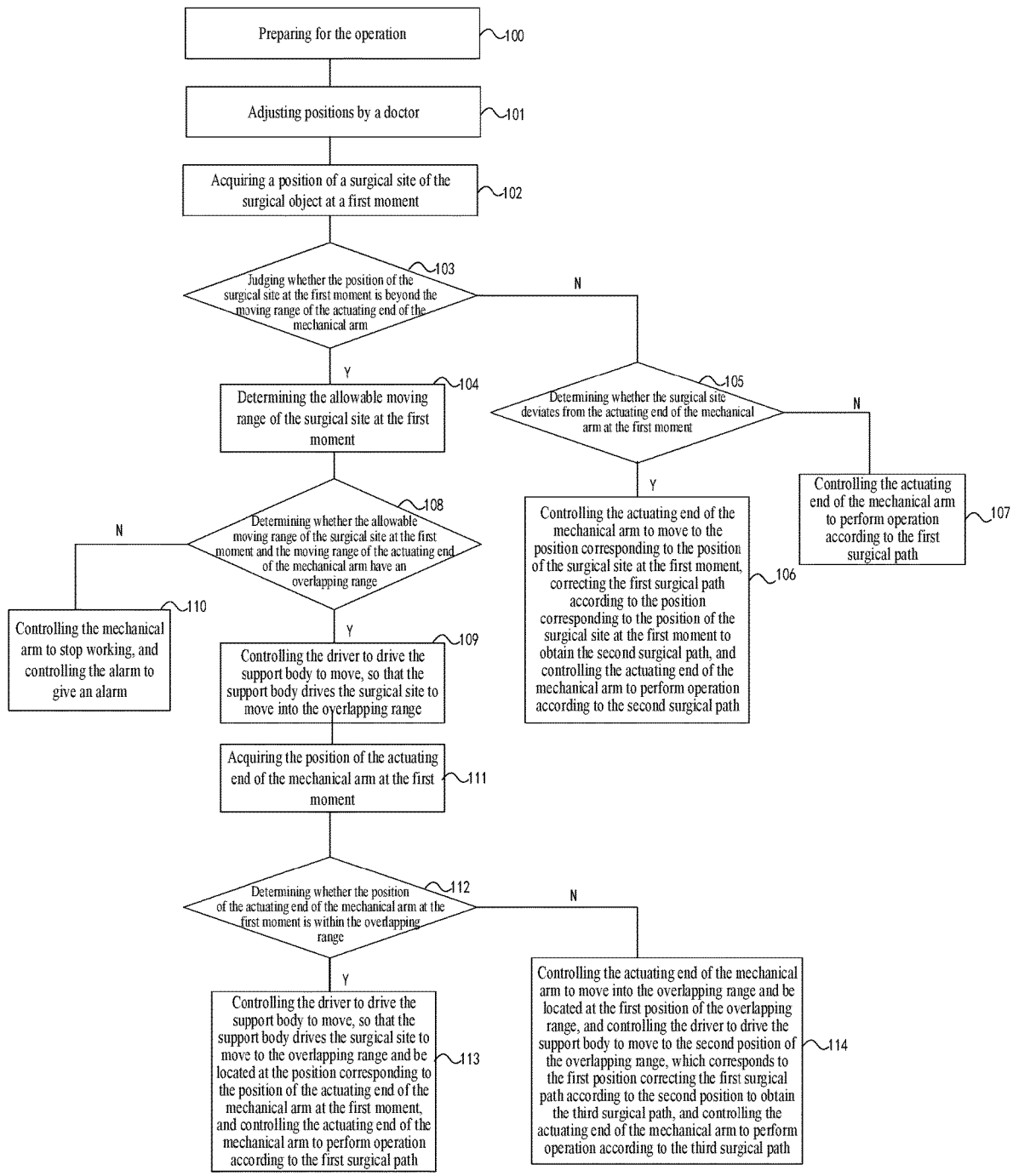
FIG. 18 is a flowchart of another surgical operation monitoring method provided by an embodiment of the disclosure.

Before the operation starts, the surgical support device 1 and the surgical robot 2 can be manually positioned so that the surgical site 101 of the surgical object 100 is located within the moving range of the actuating end 210 of the mechanical arm 21. At this point, the position where the support body 12 is located can be marked as a reference position. An execution body of the surgical operation monitoring method can be the surgical operation monitoring device 4 or the processor 31 shown in FIG. 4. As shown in FIGS. 17 and 18, the surgical operation monitoring method may comprise:

S102, acquiring a position of the surgical site 101 of the surgical object 100 at a first moment.

The position of the surgical site 101 of the surgical object 100 at the first moment can be acquired by the positioning and navigation device 5 in the surgical operation monitoring system described above.

By way of example, as shown in FIGS. 3 and 5, the coordinates of the surgical site 101 of the surgical object 100 in the navigation coordinate system at the first moment can be obtained by the positioning and navigation device 5, and then the coordinates of the surgical site 105 of the surgical object 100 in the navigation coordinate system at the first moment can be converted into coordinates in the world coordinate system by the processor 31, so that the position of the surgical site 101 at the first moment can be obtained. One can refer to the relevant description of the above surgical operation monitoring system for the specific implementation mode, which will not be repeated here.

S104, under the condition that the position of the surgical site 101 at the first moment exceeds a moving range of the actuating end 210 of the mechanical arm 21, determining an allowable moving range F2 of the surgical site 101 at the first moment, which is a range within which the driver 13 can drive the support body 12 to move so that the support body 12 drives the surgical site 101 to move at the first moment.

For example, the number of the drivers 13 is at least three, and the at least three drivers include a first driver, a second driver and a third driver. The allowable moving range F2 may be a range defined by a first allowable moving range in the first direction, a second allowable moving range in the second direction and a third allowable moving range in the third direction. One can also refer to the relevant description of the allowable moving range F2 in the above surgical operation monitoring system for the specific implementation mode, which will not be repeated here.

S109, under the condition that the allowable moving range F2 of the surgical site 101 at the first moment and the moving range F1 of the actuating end 210 of the mechanical arm 21 have an overlapping range F3, controlling the driver 13 to drive the support body 12 to move so that the support body 12 drives the surgical site 101 to move into the overlapping range F3.

When the moving range F1 of the actuating end 210 of the mechanical arm 21 and the allowable moving range F2 of the surgical site 101 at the first moment are both represented by a coordinate range of three-dimensional coordinates, the overlapping range F3 is a range limited by the overlapping range in each direction. For details, please refer to the above description of the overlapping range F3 in the surgical operation monitoring system.

In some embodiments, the surgical operation monitoring method further comprises: S106, controlling the actuating end 210 of the mechanical arm 21 to move to a position corresponding to the position of the surgical site 101 at the first moment when the position of the surgical site 101 at the first moment does not exceed the moving range F1 of the actuating end 210 of the mechanical arm 21 and the surgical site 101 deviates from the actuating end 210 of the mechanical arm 21 at the first moment.

The expression that the surgical site 101 does not deviate from the actuating end 210 of the mechanical arm 21 at the first moment means that, at the first moment, the deviation of the surgical site 101 from the actuating end 210 of the mechanical arm 21 is within an operable range F4, so that the actuating end 210 of the mechanical arm 21 can perform operation on the surgical site 101. On the contrary, the expression that the surgical site 101 deviates from the actuating end 210 of the mechanical arm 21 at the first moment means that, at the first moment, the deviation of the surgical site 101 from the actuating end 210 of the mechanical arm 21 is beyond the operable range F4, so that the actuating end 210 of the mechanical arm 21 cannot perform operation on the surgical site 101.

In this case, the position corresponding to the position of the surgical site 101 at the first moment refers to a position where the actuating end 210 of the mechanical arm 21 can perform operation on the surgical site 101 at the first moment. The deviation between the corresponding position and the position of the surgical site 101 at the first moment is within the operable range F4.

In some other embodiments, the surgical operation monitoring method further comprises: S107, controlling the actuating end 210 of the mechanical arm 21 to perform operation according to a first surgical path when the position of the surgical site 101 at the first moment does not exceed the moving range of the actuating end 210 of the mechanical arm 21 and the surgical site 101 does not deviate from the actuating end 210 of the mechanical arm 21 at the first moment; and S106, correcting the first surgical path according to the position corresponding to the position of the surgical site 101 at the first moment to obtain a second surgical path when the position of the surgical site 101 at the first moment does not exceed the moving range F1 of the actuating end 210 of the mechanical arm 21 and the surgical site 101 deviates from the actuating end 210 of the mechanical arm 21 at the first moment, and controlling the actuating end 210 of the mechanical arm 21 to perform operation according to the second surgical path after the actuating end 210 of the mechanical arm 21 moves to the position corresponding to the position of the surgical site 101 at the first moment.

In these embodiments, the first surgical path may be a preset path. That is to say, before surgery, an attending doctor plans the surgical path according to the surgical site and stores it in the processor, and in surgery, the doctor only needs to control the actuating end 210 of the mechanical arm 21 to perform operation according to the stored surgical path.

It should be noted that, in surgery, if the position of the surgical site 101 at the first moment does not exceed the moving range F1 of the actuating end 210 of the mechanical arm 21, and the surgical site 101 deviates from the actuating end 210 of the mechanical arm 21 at the first moment, the previous path (first surgical path) cannot be used for the operation. In this case, the surgical path needs to be adjusted according to the position corresponding to the position of the surgical site 101 at the first moment.

In some embodiments, correcting the first surgical path according to the position corresponding to the position of the surgical site 101 at the first moment may comprise:

taking the position corresponding to the position of the surgical site 101 at the first moment as a starting point, and controlling the actuating end 210 of the mechanical arm 21 to continue the operation according to a path parallel to the first surgical path, so as to correct the first surgical path, wherein a movement path of the actuating end 210 of the mechanical arm 21 from the starting point is the second surgical path.

In other embodiments, the surgical operation monitoring method further comprises: acquiring a first deviation of the surgical site 101 from the actuating end 210 of the mechanical arm 21 at a first moment. If the first deviation is within the operable range F4, the surgical site 101 does not deviate from the actuating end 210 of the mechanical arm 21, and if the first deviation is beyond the operable range F4, the surgical site 101 deviates from the actuating end 210 of the mechanical arm 21.

In other embodiments, the surgical operation monitoring method further comprises: S111, acquiring the position of the actuating end 210 of the mechanical arm 21 at the first moment; and S113, controlling the driver 13 to drive the support body 12 to move to make the support body 12 drive the surgical site to move into the overlapping range F3 when the position of the surgical site 101 at the first moment exceeds the moving range F1 of the actuating end 210 of the mechanical arm 21 and the position of the actuating end 210 of the mechanical arm 21 at the first moment is within the overlapping range F3, including controlling the driver 13 to drive the support body 12 to move, so that the support body 12 drives the surgical site 101 to move to a position corresponding to the position of the actuating end 210 of the mechanical arm 21 at the first moment.

In this embodiment, the position corresponding to the position of the actuating end 210 of the mechanical arm 21 at the first moment refers to the position where the actuating end 210 of the mechanical arm 21 can perform operation on the surgical site 101 at the first moment. The deviation between the corresponding position and the position of the surgical site 101 at the first moment is within the operable range F4.

In other embodiments, the surgical operation monitoring method further comprises: S114, when the position of the actuating end 210 of the mechanical arm 21 at the first moment is beyond the overlapping range F3, controlling the actuating end 210 of the mechanical arm 21 to move to the first position within the overlapping range F3. Controlling the driver 13 to drive the support body 12 to move so that the support body 12 drives the surgical site 101 to move into the overlapping range F3 comprises: controlling the driver 13 to drive the support body 12 to move so that the support body 12 drives the surgical site 101 to move to the second position in the overlapping range F3, and the second position is a position corresponding to the first position.

The second position is a position corresponding to the first position, which means that when the actuating end 210 of the mechanical arm 21 is in the first position, the second position is a position where the actuating end 210 of the mechanical arm 21 can perform surgical operation on the surgical site 101. At this corresponding position, the deviation of the surgical site 101 relative to the actuating end 210 of the mechanical arm 21 is within the operable range F4.

In yet other embodiments, the surgical operation monitoring method further comprises: S113, controlling the actuating end 210 of the mechanical arm 21 to perform operation according to the first surgical path after the support body 12 drives the surgical site 101 to move to the position corresponding to the position of the actuating end 210 of the mechanical arm 21 at the first moment when the position of the actuating end 210 of the mechanical arm 21 is located within the overlapping range F3; and S114, correcting the first surgical path according to the first position to obtain a third surgical path and controlling the actuating end 210 of the mechanical arm 21 to perform operation according to the third surgical path when the position of the actuating end 210 of the mechanical arm 21 at the first moment is beyond the overlapping range F3.

In these embodiments, the first surgical path may be a preset path. That is to say, before surgery, an attending doctor plans the surgical path according to the surgical site 101 and stores it in the processor 31, and in surgery, the doctor only needs to control the actuating end 210 of the mechanical arm 21 to perform operation according to the stored surgical path.

It should be noted that if the surgical site 101 deviates from the actuating end 210 of the mechanical arm 21 at the first moment in surgery, the previous path (first surgical path) cannot be used for the operation, that is, the deviation of the surgical site 101 from the actuating end 210 of the mechanical arm 21 exceeds the operable range F4, the actuating end 210 of the mechanical arm 21 is controlled to move to the first position within the overlapping range F3, and the driver 13 is controlled to drive the support body 12 to move so that the support body 12 drives the surgical site 101 to move to the second position within the overlapping range F3, the surgical path needs to be adjusted according to the second position.

In some embodiments, correcting the first surgical path according to the second position may comprise:

taking the second position as a starting point, and controlling the actuating end 210 of the mechanical arm 21 to continue the operation according to a path parallel to the first surgical path, so as to correct the first surgical path, wherein a movement path of the actuating end 210 of the mechanical arm 21 from the starting point is the third surgical path.

In yet other embodiments, the mechanical arm 21 is controlled to stop moving and an alarm is controlled to give an alarm when the position of the surgical site 101 exceeds the moving range F1 of the actuating end 210 of the mechanical arm 21 and the allowable moving range F2 of the surgical site at the first moment and the moving range F1 of the actuating end 210 of the mechanical arm 21 do not have an overlapping range F3 31. That is, the operation can be suspended at this point, and resumed by manually adjusting the position of the support body 12.

In order to describe the flow of the whole surgical operation monitoring method more clearly, explanation will be made with reference to FIG. 18 by a specific embodiment.

S100, preparing for the operation.

Before the operation starts, the positions of the surgical support device 1 and the surgical robot 2 are manually adjusted, that is, S101, adjusting, by a doctor, the positions so that the surgical site 101 of the surgical object 100 is located within the moving range F1 of the actuating end 210 of the mechanical arm 21.

Then, the operation is started, specifically, the operation is performed according to the first surgical path by controlling the actuating end 210 of the mechanical arm 21, and the first surgical path can be a preset path set by calculation before the operation starts.

In this process, the position of the surgical site of the surgical object is monitored in real time. Specifically:

S102, acquiring the position of the surgical site of the surgical object at the first moment, wherein the first moment is any moment in the surgical process.

In the operation process, S103, judging whether the position of the surgical site at the first moment is beyond the moving range of the actuating end of the mechanical arm; if yes, S104, determining the allowable moving range F2 of the surgical site 101 at the first moment, and if not, S105, determining whether the surgical site 101 deviates from the actuating end of the mechanical arm 21 at the first moment; if so, S106, controlling the actuating end 210 of the mechanical arm 21 to move to the position corresponding to the position of the surgical site 101 at the first moment, correcting the first surgical path according to the position corresponding to the position of the surgical site 101 at the first moment to obtain the second surgical path, and controlling the actuating end 210 of the mechanical arm 21 to perform operation according to the second surgical path, and if not, S107, controlling the actuating end 210 of the mechanical arm 21 to perform operation according to the first surgical path.

After the position of the surgical site at the first moment is beyond the moving range of the actuating end of the mechanical arm, and the allowable moving range F2 of the surgical site at the first moment is determined, S108, determining whether the allowable moving range F2 of the surgical site at the first moment and the moving range F1 of the actuating end 210 of the mechanical arm 21 have an overlapping range F3; if yes, S109, controlling the driver 13 to drive the support body 12 to move, so that the support body 12 drives the surgical site 101 to move into the overlapping range F3, and if not, S110, controlling the mechanical arm 21 to stop working, controlling the alarm to give an alarm, returning to the beginning to adjust the positions by manual operation, and repeating the above steps to perform operation again.

If it is determined that the allowable moving range F2 of the surgical site at the first moment and the moving range F1 of the actuating end 210 of the mechanical arm 21 have an overlapping range F3, S111, acquiring the position of the actuating end 210 of the mechanical arm 21 at the first moment; S112, determining whether the position of the actuating end 210 of the mechanical arm 21 at the first moment is within the overlapping range F3; if yes, S113, controlling the driver 13 to drive the support body to move, so that the support body 12 drives the surgical site to move to the overlapping range F3 and be located at the position corresponding to the position of the actuating end 210 of the mechanical arm 21 at the first moment, and controlling the actuating end 210 of the mechanical arm 21 to perform operation according to the first surgical path, and if not, S114, controlling the actuating end 210 of the mechanical arm to move into the overlapping range F3 and be located at the first position of the overlapping range F3, controlling the driver 13 to drive the support body 12 to move to the second position of the overlapping range, which corresponds to the first position, correcting the first surgical path according to the second position to obtain the third surgical path, and controlling the actuating end 210 of the mechanical arm 21 to perform operation according to the third surgical path. In this way, a monitoring process is completed, and the operation is continuously monitored according to the above steps until the operation is completed.

In the embodiments of this application, because the steps in the above-mentioned surgical operation monitoring method are similar to the functions realized by the surgical operation monitoring device, one can refer to the relevant description of the surgical operation monitoring device in the above-mentioned embodiment for specific implementation of the method, which will not be described in detail here. Accordingly, the surgical operation monitoring method has the same technical effect as the surgical operation monitoring device.

Figure 19:
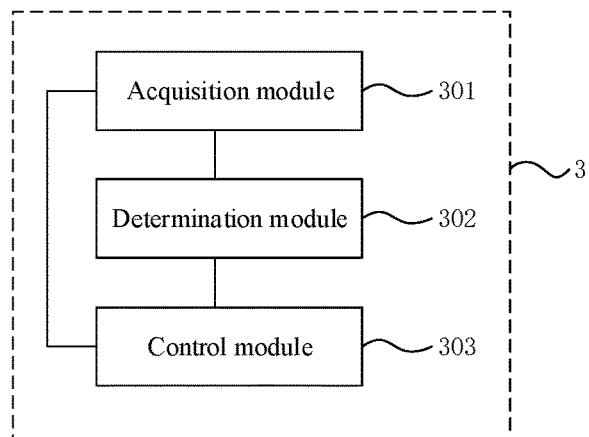
FIG. 19 is a structural block diagram of a surgical operation monitoring device provided by an embodiment of the disclosure.

An embodiment of the disclosure provides a surgical operation monitoring device. As shown in FIG. 19, the surgical operation monitoring device 3 comprises an acquisition module 301, a determination module 302 and a control module 303.

The acquisition module 301 is configured to acquire a position of a surgical site of a surgical object at a first moment.

The determination module 302 is configured to, under the condition that the position of the surgical site at the first moment exceeds a moving range of an actuating end of a mechanical arm, determine an allowable moving range of the surgical site at the first moment, which is a range within which a driver can drive a support body to move so that the support body drives the surgical site to move at the first moment.

The control module 303 is configured to, under the condition that the allowable moving range of the surgical site at the first moment and the moving range of the actuating end of the mechanical arm have an overlapping range, control the driver to drive the support body to move so that the support body drives the surgical site to move into the overlapping range.

In some embodiments, the control module 303 is further configured to control the actuating end of the mechanical arm to move to a position corresponding to the position of the surgical site at the first moment when the position of the surgical site at the first moment does not exceed the moving range of the actuating end of the mechanical arm and the surgical site deviates from the mechanical arm at the first moment.

In some embodiments, the control module 303 is further configured to control the actuating end of the mechanical arm to perform operation according to a first surgical path when the position of the surgical site at the first moment does not exceed the moving range F1 of the actuating end of the mechanical arm and the surgical site does not deviate from the actuating end of the mechanical arm at the first moment, correct the first surgical path according to the position corresponding to the position of the surgical site at the first moment to obtain a second surgical path when the position of the surgical site at the first moment does not exceed the moving range of the actuating end of the mechanical arm and the surgical site deviates from the actuating end of the mechanical arm at the first moment, and control the actuating end of the mechanical arm to perform operation according to the second surgical path after the actuating end of the mechanical arm moves to the position corresponding to the position of the surgical site at the first moment.

In some embodiments, the acquisition module 301 is further configured to acquire a first deviation of the surgical site from the actuating end 210 of the mechanical arm at a first moment. If the first deviation is within the operable range F4, the surgical site does not deviate from the actuating end of the mechanical arm, and if the first deviation is beyond the operable range F4, the surgical site deviates from the actuating end of the mechanical arm.

In some embodiments, the acquisition module 301 is further configured to acquire the position of the actuating end of the mechanical arm at the first moment. The control module 303 is specifically configured to control the driver to drive the support body to move, so that the support body drives the surgical site to move to a position corresponding to the position of the actuating end of the mechanical arm at the first moment when the position of the surgical site at the first moment exceeds the moving range of the actuating end of the mechanical arm and the position of the actuating end of the mechanical arm at the first moment is within the overlapping range.

In some embodiments, the control module 303 is further configured to control the actuating end of the mechanical arm to move to a first position within the overlapping range F3 when the position of the actuating end of the mechanical arm at the first moment is beyond the overlapping range, and is specifically configured to control the driver to drive the support body to move, so that the support body drives the surgical site to move to a second position within the overlapping range, and the second position is a position corresponding to the first position.

In yet other embodiments, the control module 303 is further configured to control the actuating end of the mechanical arm to perform operation according to the first surgical path after the support body drives the surgical site to move to the position corresponding to the position of the actuating end of the mechanical arm at the first moment when the position of the actuating end of the mechanical arm is located within the overlapping range, correct the first surgical path according to a second position to obtain a third surgical path and control the actuating end of the mechanical arm to perform operation according to the third surgical path when the position of the actuating end of the mechanical arm at the first moment is beyond the overlapping range.

In some embodiments, the control module 303 is further configured to control the mechanical arm to stop moving and control the alarm to give an alarm when the position of the surgical site exceeds the moving range of the actuating end of the mechanical arm and the allowable moving range of the surgical site at the first moment and the moving range of the actuating end of the mechanical arm do not have an overlapping range.

The device embodiment described in FIG. 19 is only schematic. For example, the above module division is only based on logical functions. In actual implementation, there may be other division modes, for example, multiple modules or components can be combined or integrated into another system, or some features can be ignored or not executed. The functional modules in the embodiments of this application can be integrated into one processing module, or each module can individually exist physically, or two or more modules can be integrated into one module. The above modules in FIG. 4 can be implemented in the form of hardware or in the form of software functional units. For example, when implemented in the form of software, the above-mentioned acquisition module 301, determination module 302 and control module 303 can be realized by software functional modules generated after at least one processor 31 in FIG. 4 reads program codes stored in a memory 32. The above modules in FIG. 19 can also be implemented by different types of hardware in the surgical operation monitoring device, for example, the acquisition module 301 and the determination module 302 are implemented by part of processing resources (such as one core or two cores in a multi-core processor) in the at least one processor 31 in FIG. 4, and the control module 303 is implemented by the rest of processing resources (such as other cores in the multi-core processor) in the at least one processor 31 in FIG. 4, or realized by programmable devices such as field-programmable gate array (FPGA) or coprocessor. Obviously, the above functional modules can also be realized by combining software and hardware. For example, the acquisition module 301 is realized by a hardware programmable device, and the detection and determination module 302 and the processing control module 303 are software functional modules generated after a CPU reads the program codes stored in the memory 32.

For more details on how the acquisition module 301, the determination module 302 and the control module 303 in FIG. 19 realize the above functions, please refer to the relevant description in the previous embodiments, which will not be repeated here. The surgical operation monitoring device also has the same technical effect as the surgical operation monitoring device described above.

An embodiment of the disclosure also provides a computer storage medium, which stores computer program instructions, and when the computer program instructions are run on the surgical operation monitoring device, the surgical operation monitoring device is enabled to execute the surgical operation monitoring method as described above.

Figure 20:
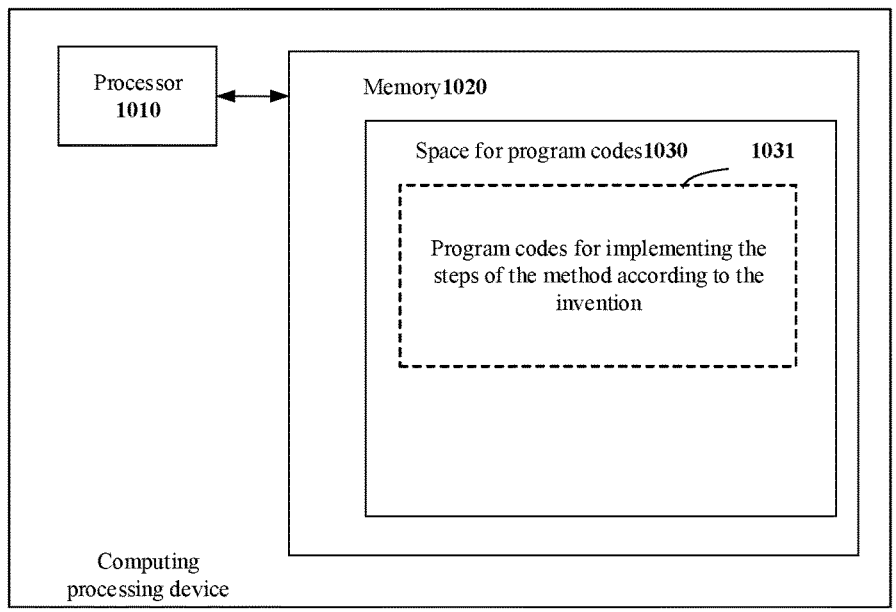
FIG. 20 schematically shows a block diagram of a surgical operation monitoring device for performing a method of the disclosure.
Figure 21:
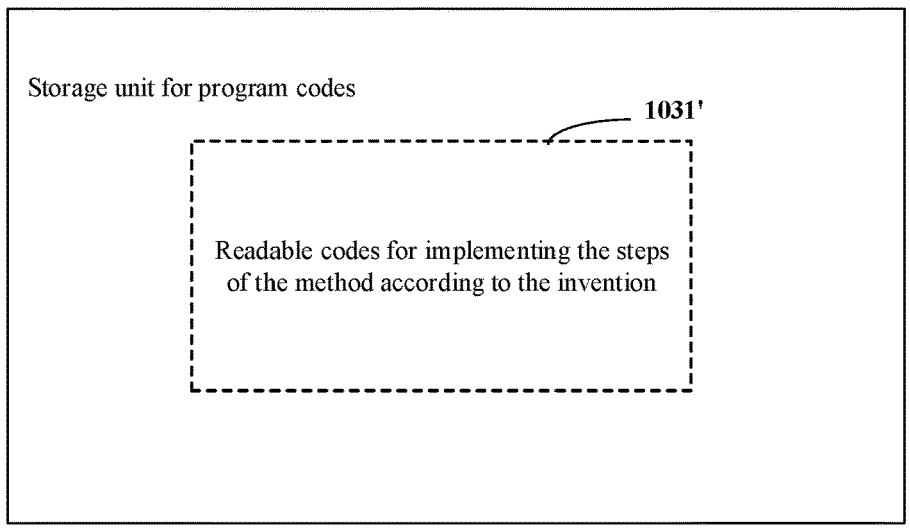
FIG. 21 schematically shows a storage unit for retaining or carrying program codes for implementing a method of the disclosure.

For example, FIG. 20 shows a surgical operation monitoring device which can implement the method according to the disclosure. The surgical operation monitoring device conventionally comprises a processor 1010 and a computer program product or computer readable medium in the form of a memory 1020. The memory 1020 may be an electronic memory such as flash memory, EEPROM (electrically erasable programmable read only memory), EPROM, hard disk or ROM. The memory 1020 has storage spaces 1030 for program codes 1031 for executing any step in the above method. For example, the storage spaces 1030 for the program codes may contain various program codes 1031 for implementing the steps in the above method. These program codes can be read from or written into one or more computer program products. These computer program products include program code carriers such as hard disk, compact disk (CD), memory card or floppy disk. Such a computer program product is usually a portable or fixed storage unit as described with reference to FIG. 21. The storage unit may have memory segments, memory spaces, and the like arranged similarly to the memory 1020 in the surgical operation monitoring device of FIG. 20. The program codes can be compressed in an appropriate form, for example. Generally, the storage unit contains computer readable codes 1031', i.e., codes readable by, for example, a processor such as 1010, which, when run by the surgical operation monitoring device, cause the surgical operation monitoring device to implement the steps in the method described above.

All the embodiments in this specification are described in a progressive way, and the same and similar parts of different embodiments can serve as references for each other. Each embodiment focuses on its differences from other embodiments.

The above embodiments can be implemented in whole or in part by software, hardware, firmware or any combination thereof. When implemented by using a software program, the embodiments can be fully or partially implemented in the form of computer program products. The computer program product includes one or more computer program instructions. When the computer program instructions are loaded and executed on a computer, all or part of the flow or function of the embodiment of the application is generated. The computer can be a general purpose computer, a special purpose computer, a computer network or other programmable devices. The computer program instructions can be transmitted from one website, computer, server or data center to another web site, computer, server or data center in a wired manner (such as coaxial cable, optical fiber, digital subscriber line (DSL)) or wireless manner (such as infrared, wireless, microwave). The computer-readable storage medium can be any available medium that can be accessed by a computer or a data storage device including one or more servers, data centers and the like integrated with available media. The available medium can be magnetic medium (e.g., floppy disk, magnetic disk, magnetic tape), optical medium (e.g., digital video disc (DVD)), or semiconductor medium (e.g., solid state drives (SSD)), etc.

The protection scope of the disclosure is not limited to the above description. Anyone skilled in the art can easily think of changes or substitutions within the technical scope disclosed in the disclosure, which should be covered within the protection scope of the disclosure. Therefore, the protection scope of the disclosure shall be subject to the protection scope of the claims.

The invention claimed is:

1. A surgical operation monitoring method, applied to a surgical operation monitoring system, wherein the surgical operation monitoring system comprises a surgical support device and a surgical robot, the surgical support device comprises a stand, a support body mounted on the stand and a driver configured to drive the support body to move relative to the stand, the support body is configured to support a surgical object, and the surgical robot comprises mechanical arms with actuating ends; and the surgical operation monitoring method comprises:
acquiring a position of a surgical site of the surgical object at a first moment;
under the condition that the position of the surgical site at the first moment exceeds a moving range of the actuating end of the mechanical arm, determining an allowable moving range of the surgical site at the first moment, which is a range within which the driver is capable of driving the support body to move so that the support body drives the surgical site to move at the first moment; and
under the condition that the allowable moving range of the surgical site at the first moment and the moving range of the actuating end of the mechanical arm have an overlapping range, controlling the driver to drive the support body to move so that the support body drives the surgical site to move into the overlapping range;
controlling the actuating end of the mechanical arm to perform operation according to a first surgical path, under the condition that the position of the surgical site at the first moment does not exceed the moving range of the actuating end of the mechanical arm and the surgical site does not deviate from the actuating end of the mechanical arm at the first moment; and
correcting the first surgical path according to a position corresponding to the position of the surgical site at the first moment to obtain a second surgical path, under the condition that the position of the surgical site at the first moment does not exceed the moving range of the actuating end of the mechanical arm and the surgical site deviates from the actuating end of the mechanical arm at the first moment, and controlling the actuating end of the mechanical arm to perform operation according to the second surgical path after the actuating end of the mechanical arm moves to the position corresponding to the position of the surgical site at the first moment.

2. The surgical operation monitoring method according to claim 1, wherein the method further comprises:
controlling the actuating end of the mechanical arm to move to a position corresponding to the position of the surgical site at the first moment, under the condition that the position of the surgical site at the first moment does not exceed the moving range of the actuating end of the mechanical arm and the surgical site deviates from the actuating end of the mechanical arm at the first moment.

3. The surgical operation monitoring method according to claim 2, wherein the method further comprises:
acquiring a first deviation of the surgical site from the actuating end of the mechanical arm at the first moment;
wherein, if the first deviation is within an operable range, the surgical site does not deviate from the actuating end of the mechanical arm; and if the first deviation is beyond the operable range, the surgical site deviates from the actuating end of the mechanical arm.

4. The surgical operation monitoring method according to claim 1, wherein the method further comprises:
acquiring a position of the actuating end of the mechanical arm at the first moment; and
controlling the driver to drive the support body to move to make the support body drive the surgical site to move into the overlapping range, under the condition that the position of the surgical site at the first moment exceeds the moving range of the actuating end of the mechanical arm and the position of the actuating end of the mechanical arm at the first moment is within the overlapping range, comprising: controlling the driver to drive the support body to move, so that the support body drives the surgical site to move to a position corresponding to the position of the actuating end of the mechanical arm at the first moment.

5. The surgical operation monitoring method according to claim 1, wherein the method further comprises:
controlling the actuating end of the mechanical arm to move to a first position within the overlapping range, under the condition that the position of the actuating end of the mechanical arm at the first moment is beyond the overlapping range; and
controlling the driver to drive the support body to move so that the support body drives the surgical site to move into the overlapping range comprises:
controlling the driver to drive the support body to move, so that the support body drives the surgical site to move to a second position within the overlapping range, the second position being a position corresponding to the first position.

6. The surgical operation monitoring method according to claim 4, wherein the method further comprises:
controlling the actuating end of the mechanical arm to perform operation according to a first surgical path after the support body drives the surgical site to move to the position corresponding to the position of the actuating end of the mechanical arm at the first moment under the condition that the position of the actuating end of the mechanical arm is located within the overlapping range; and correcting the first surgical path according to the first position to obtain a third surgical path and controlling the actuating end of the mechanical arm to perform operation according to the third surgical path, under the condition that the position of the actuating end of the mechanical arm at the first moment is beyond the overlapping range.

7. The surgical operation monitoring method according to claim 1, wherein the surgical operation monitoring system further comprises an alarm, and the surgical operation monitoring method further comprises:

controlling the mechanical arm to stop moving and controlling the alarm to give an alarm, under the condition that the position of the surgical site exceeds the moving range of the actuating end of the mechanical arm and the allowable moving range of the surgical site at the first moment and the moving range of the actuating end of the mechanical arm do not have an overlapping range.

8. The surgical operation monitoring method according to claim 1, wherein, the number of the drivers is at least three, and the at least three drivers comprise a first driver, a second driver and a third driver; the first driver is configured to drive the support body to move in a first direction, the second driver is configured to drive the support body to move in a second direction, the third driver is configured to drive the support body to move in a third direction, and the first direction, the second direction and the third direction are perpendicular to each other;

acquiring the position of the surgical site at the first moment comprises:

acquiring the coordinates of the surgical site at the first moment; and determining the allowable moving range of the surgical site at the first moment comprises:

acquiring a first allowable deviation distance in the first direction, a second allowable deviation distance in the second direction and a third allowable deviation distance in the third direction of the support body at the first moment; and according to the first allowable deviation distance, the second allowable deviation distance and the third allowable deviation distance, and the coordinates of the surgical site at the first moment, calculating the coordinates of the surgical site after the surgical site deviates by the first allowable deviation distance in the first direction, the second allowable deviation distance in the second direction and the third allowable deviation distance in the third direction, to determine that a range defined by the coordinates of the surgical site after the surgical site deviates by the first allowable deviation distance in the first direction, the second allowable deviation distance in the second direction and the third allowable deviation distance in the third direction is the allowable movement range.

9. The surgical operation monitoring method according to claim 8, wherein the surgical operation monitoring system further comprises at least three position sensors, and the at least three position sensors comprise a first position sensor, a second position sensor and a third position sensor which are electrically connected with the processor; the first position sensor is configured to detect a first deviation distance of the support body relative to a reference position in the first direction, the second position sensor is configured to detect a second deviation distance of the support body relative to the reference position in the second direction, and the third position sensor is configured to detect a third deviation distance of the support body relative to the reference position in the third direction; and acquiring the first allowable deviation distance in the first direction, the second allowable deviation distance in the second direction and the third allowable deviation distance in the third direction of the support body at the first moment comprises:

receiving the first deviation distance, the second deviation distance and the third deviation distance detected by the first position sensor, the second position sensor and the third position sensor; and according to the received first deviation distance, second deviation distance and third deviation distance, and a first deviatable distance in the first direction, a second deviatable distance in the second direction and a third deviatable distance in the third direction of the support body when the support body is located at the reference position, calculating the first allowable deviation distance in the first direction, the second allowable deviation distance in the second direction and the third allowable deviation distance in the third direction of the support body at the first moment.

10. A surgical operation monitoring device, comprising: a processor and a non-transitory memory, wherein the non-transitory memory is configured to store computer program instructions; and when the computer program instructions are executed by the processor, the surgical operation monitoring device is caused to implement the operations comprising:

acquiring a position of a surgical site of the surgical object at a first moment;

under the condition that the position of the surgical site at the first moment exceeds a moving range of the actuating end of the mechanical arm, determining an allowable moving range of the surgical site at the first moment, which is a range within which the driver is capable of driving the support body to move so that the support body drives the surgical site to move at the first moment; and under the condition that the allowable moving range of the surgical site at the first moment and the moving range of the actuating end of the mechanical arm have an overlapping range, controlling the driver to drive the support body to move so that the support body drives the surgical site to move into the overlapping range;

controlling the actuating end of the mechanical arm to perform operation according to a first surgical path, under the condition that the position of the surgical site at the first moment does not exceed the moving range of the actuating end of the mechanical arm and the surgical site does not deviate from the actuating end of the mechanical arm at the first moment; and correcting the first surgical path according to a position corresponding to the position of the surgical site at the first moment to obtain a second surgical path, under the condition that the position of the surgical site at the first moment does not exceed the moving range of the actuating end of the mechanical arm and the surgical site deviates from the actuating end of the mechanical arm at the first moment, and controlling the actuating end of the mechanical arm to perform operation according to the second surgical path after the actuating end of the mechanical arm moves to the position corresponding to the position of the surgical site at the first moment.

11. The surgical operation monitoring device according to claim 10, wherein the operations further comprise:
controlling the actuating end of the mechanical arm to move to a position corresponding to the position of the surgical site at the first moment, under the condition that the position of the surgical site at the first moment does not exceed the moving range of the actuating end of the mechanical arm and the surgical site deviates from the actuating end of the mechanical arm at the first moment.

12. The surgical operation monitoring device according to claim 11, wherein the operations further comprise:
acquiring a first deviation of the surgical site from the actuating end of the mechanical arm at the first moment;
wherein, if the first deviation is within an operable range, the surgical site does not deviate from the actuating end of the mechanical arm; and if the first deviation is beyond the operable range, the surgical site deviates from the actuating end of the mechanical arm.

13. The surgical operation monitoring device according to claim 10, wherein the operations further comprise:
acquiring a position of the actuating end of the mechanical arm at the first moment; and
controlling the driver to drive the support body to move to make the support body drive the surgical site to move into the overlapping range, under the condition that the position of the surgical site at the first moment exceeds the moving range of the actuating end of the mechanical arm and the position of the actuating end of the mechanical arm at the first moment is within the overlapping range, comprising: controlling the driver to drive the support body to move, so that the support body drives the surgical site to move to a position corresponding to the position of the actuating end of the mechanical arm at the first moment.

14. The surgical operation monitoring device according to claim 10, wherein the operations further comprise:
controlling the actuating end of the mechanical arm to move to a first position within the overlapping range, under the condition that the position of the actuating end of the mechanical arm at the first moment is beyond the overlapping range; and
controlling the driver to drive the support body to move so that the support body drives the surgical site to move into the overlapping range comprises:
controlling the driver to drive the support body to move, so that the support body drives the surgical site to move to a second position within the overlapping range, the second position being a position corresponding to the first position.

15. A non-transitory computer readable storage medium, which stores computer program instructions, wherein when the computer program instructions are run on a surgical operation monitoring device, the surgical operation monitoring device is enabled to execute the operations comprising:
acquiring a position of a surgical site of the surgical object at a first moment;

under the condition that the position of the surgical site at the first moment exceeds a moving range of the actuating end of the mechanical arm, determining an allowable moving range of the surgical site at the first moment, which is a range within which the driver is capable of driving the support body to move so that the support body drives the surgical site to move at the first moment; and under the condition that the allowable moving range of the surgical site at the first moment and the moving range of the actuating end of the mechanical arm have an overlapping range, controlling the driver to drive the support body to move so that the support body drives the surgical site to move into the overlapping range;

controlling the actuating end of the mechanical arm to perform operation according to a first surgical path, under the condition that the position of the surgical site at the first moment does not exceed the moving range of the actuating end of the mechanical arm and the surgical site does not deviate from the actuating end of the mechanical arm at the first moment; and correcting the first surgical path according to a position corresponding to the position of the surgical site at the first moment to obtain a second surgical path, under the condition that the position of the surgical site at the first moment does not exceed the moving range of the actuating end of the mechanical arm and the surgical site deviates from the actuating end of the mechanical arm at the first moment, and controlling the actuating end of the mechanical arm to perform operation according to the second surgical path after the actuating end of the mechanical arm moves to the position corresponding to the position of the surgical site at the first moment.

16. The non-transitory computer readable storage medium according to claim 15, wherein the operations further comprise:
controlling the actuating end of the mechanical arm to move to a position corresponding to the position of the surgical site at the first moment, under the condition that the position of the surgical site at the first moment does not exceed the moving range of the actuating end of the mechanical arm and the surgical site deviates from the actuating end of the mechanical arm at the first moment.

17. The non-transitory computer readable storage medium according to claim 16, wherein the operations further comprise:
acquiring a first deviation of the surgical site from the actuating end of the mechanical arm at the first moment;
wherein, if the first deviation is within an operable range, the surgical site does not deviate from the actuating end of the mechanical arm; and if the first deviation is beyond the operable range, the surgical site deviates from the actuating end of the mechanical arm.

* * * * *